(12) United States Patent
Baughman et al.

(10) Patent No.: US 11,608,519 B2
(45) Date of Patent: *Mar. 21, 2023

(54) SPECIFIC DETECTION OF DEOXYRIBONUCLEIC ACID SEQUENCES USING NOVEL CRISPR ENZYME-MEDIATED DETECTION STRATEGIES

(71) Applicant: TOKITAE LLC, Bellevue, WA (US)

(72) Inventors: Ted A. Baughman, Redmond, WA (US); Damian Madan, Issaquah, WA (US); Eric Nalefski, Bainbridge Island, WA (US); Anne-Laure M. Le Ny, Issaquah, WA (US)

(73) Assignee: Tokitae LLC, Bellevue, WA (US)

( * ) Notice: Subject to any disclaimer, the term of this patent is extended or adjusted under 35 U.S.C. 154(b) by 695 days.

This patent is subject to a terminal disclaimer.

(21) Appl. No.: 16/049,460

(22) Filed: Jul. 30, 2018

(65) Prior Publication Data

US 2020/0032325 A1 Jan. 30, 2020

(51) Int. Cl.
*C12Q 1/6832* (2018.01)
*C12N 9/22* (2006.01)
*C12N 15/11* (2006.01)

(52) U.S. Cl.
CPC ............ *C12Q 1/6832* (2013.01); *C12N 9/22* (2013.01); *C12N 15/11* (2013.01); *C12N 2310/20* (2017.05); *C12N 2800/80* (2013.01)

(58) Field of Classification Search
CPC ........ C12Q 1/6832; C12N 9/22; C12N 15/11; C12N 2310/20; C12N 2800/80
See application file for complete search history.

(56) References Cited

U.S. PATENT DOCUMENTS

| | | | |
|---|---|---|---|
| 2001/0008771 A1 | 7/2001 | Seibel et al. | |
| 2007/0128589 A1 | 6/2007 | Sanders et al. | |
| 2010/0291547 A1 | 11/2010 | Chen et al. | |
| 2014/0220589 A1 | 8/2014 | Sanders et al. | |
| 2014/0227773 A1 | 8/2014 | Babu et al. | |
| 2017/0204407 A1 | 7/2017 | Gilbert et al. | |
| 2018/0208976 A1 | 7/2018 | Doudna et al. | |
| 2018/0274017 A1 | 9/2018 | Abudayyeh et al. | |
| 2020/0032324 A1* | 1/2020 | Baughman | C12N 15/11 |
| 2020/0032325 A1 | 1/2020 | Baughman et al. | |

FOREIGN PATENT DOCUMENTS

| | | | |
|---|---|---|---|
| EP | 3325651 | A1 | 2/2020 |
| WO | 2013158505 | A1 | 10/2013 |
| WO | 2016205764 | A9 | 4/2017 |
| WO | 2018107129 | A1 | 6/2018 |
| WO | 2020028180 | A1 | 2/2020 |
| WO | 2020167597 | A1 | 8/2020 |

OTHER PUBLICATIONS

Gootenberg et al.; "Multiplexed and portable nucleic acid detection platform with Cas13, Cas12a, and Csm6"; Science; Apr. 27, 2018; pp. 439-444 (internal pp. 1-6); vol. 360. (Year: 2018).*
Gootenberg et al.; "Multiplexed and portable nucleic acid detection platform with Cas13, Cas12a, and Csm6"; Science; Apr. 27, 2018; pp. 439-444 (internal pp. 1-6); vol. 360. Supplementary Material. (Year: 2018).*
Li et al.; "CRISPR-Cas12a-assisted nucieicacid detection"; Cell Discovery; Apr. 24, 2018; pp. 1-4; vol. 4, No. 20.
Chen et al.; "CRISPR-Cas12a target binding unleashes indiscriminate single-stranded DNase activity"; Science; 10.1126/science.aar6245 (2018).
Jinek et al.; "A Programmable Dual-RNA-Guided DNA Endonuclease in Adaptive Bacterial Immunity"; Aug. 17, 2012; pp. 816-821; vol. 337.
Shmakov et al.; "Discovery and functional characterization of diverse Class 2 CRISPR-Cas systems"; Mol. Cell; Nov. 5, 2015; pp. 385-397; vol. 60, No. 3.
Abudayyeh et al.; "C2c2 Is a single-component programmable RNA-gulded RNA-targeting CRISPR effector"; Science 353; aaf5573 (2016), DOI: 10.1126/science.aaf5573.
East-Seletsky, Alexandra; "Two Distinct RNase Activities of CRISPR-C2c2 Enable Guide-RNA Processing and RNA Detection"; Nature; Oct. 13, 2016; 538(7624): 270-273. doi:10.1038/nature19802.
Madam et al.; "Non-Invasive Imaging of Tumors by Monitoring Autotaxin Activity Using an Enzyme-Activated Near-Infrared Fluorogenic Substrate"; PLOS ONE; Nov. 2013; pp. 1-9; vol. 8, Issue 11.
Gootenberg et al.; "Nucleic acid detection with CRISPR-Cas13a/C2c2"; Science; Apr. 28, 2017; pp. 438-442; vol. 356.
Tamulaitis et al.; "Programmable RNA Shredding by the Type III-A CRISPR-Cas System of *Streptococcus thermophlius*"; Nov. 20, 2014; pp. 506-517; vol. 56; Elsevier Inc.
PCT International Search Report; International App. No. PCT/US2019/043716; dated Oct. 30, 2019; pp. 1-3.

(Continued)

*Primary Examiner* — Nancy J Leith
(74) *Attorney, Agent, or Firm* — AEON Law, PLLC; Adam L. K. Philipp; Shan Liao

(57) ABSTRACT

Embodiments disclosed herein include devices, methods, and systems for direct, selective, and sensitive detection of single-stranded and double-stranded target DNA sequences from various sources using a Cas12a protein. When activated by binding a target DNA sequence, the Cas12a cleaves a tether releasing a reporter molecule that may then be detected. In some embodiments, the systems, methods, and devices may include a filter or membrane that may help to separate the tethered and untethered reporter molecules. These devices, systems, and techniques allow a user to rapidly process samples that may contain the target DNA, without needing to amplify the target sequences. These devices and methods may be used to assay a wide variety of samples and target DNA sources, for the presence or absence of target DNA sequences. Compositions and kits, useful in practicing these methods, for example detecting a target DNA in a biological sample, are also described.

23 Claims, 9 Drawing Sheets

Specification includes a Sequence Listing.

(56) References Cited

OTHER PUBLICATIONS

PCT International Search Report; International App. No. PCT/US2019/043734; dated Oct. 30, 2019; pp. 1-3.
Chen et al.; "CRISPR-Cas12a target binding unleashes indiscriminate single-stranded DNase activity"; Science; Apr. 27, 2018; pp. 436-439; vol. 360; American Association for the Advancement of Science.
Gootenberg et al.; "Multiplexed and portable nucleic acid detection platform with Cas13, Cas12a, and Csm6"; Science; Apr. 27, 2018; pp. 439-444; vol. 360; American Association for the Advancement of Science.
Gootenberg et al.; "Nucleic acid detection with CRISPR-Cas13a/C2c2"; Science; Apr. 28, 2017; pp. 438-442; vol. 356; American Association for the Advancement of Science.
Murugan et al., "The Revolution Continues: Newly Discovered Systems Expand the CRISPR-Cas Toolkit", Mol. Cell., vol. 68, Oct. 5, 2017, pp. 15-25.
European Supplementary Search Report and Search Opinion; EP Application No. 19844572.8; dated Mar. 31, 2022; 12 pages.

\* cited by examiner

SPECIFIC DETECTION OF DEOXYRIBONUCLEIC ACID SEQUENCES USING NOVEL CRISPR ENZYME-MEDIATED DETECTION STRATEGIES

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

INCORPORATION-BY-REFERENCE OF SEQUENCE LISTING

The present application is being filed along with a Sequence Listing in electronic format. The Sequence Listing is provided as a file entitled 20220128-SEQLIST-GLOB-2020013p.txt, which is 2,179 bytes in size, created and last modified on Jan. 27, 2022. The information in the accompanying Sequence Listing is incorporated by reference in its entirety into this application.

BACKGROUND

The CRISPR (clustered regulatory interspaced short palindromic repeats) system is a prokaryotic system for recognizing and modifying foreign genetic elements (e.g. plasmids, viruses, phages). Cas (CRISPR-associated) proteins, with the help of RNA sequences, recognize and cut DNA (deoxyribonucleic acid) and/or foreign RNA. Cas 12 or Cas12a, is a programmable DNA endonuclease, guided by a guide RNA, that possess both specific and non-specific endonuclease (DNase) activity. Activation of Cas12a's DNase activity requires binding a "guide RNA sequence," which then allows Cas12a to bind a complimentary double-stranded DNA (dsDNA) sequence. This is likely a first step that may result, ultimately, in cell death, limiting spread of the foreign nucleic acid.

Described herein is a sensitive, low-cost, rapid, and easy to use system for identification of specific target (or activator) sequences that may be performed without nucleic acid sequence amplification.

SUMMARY

Generally, embodiments of the present disclosure relate to devices, methods, and systems for direct, selective, and sensitive detection of target DNA sequences from various sources. These devices, systems, and techniques allow a user to rapidly process samples that may contain the target nucleic acid sequence, without needing to amplify the target sequences. Indeed, in various embodiments, the disclosed devices, methods, and systems may be useful in amplifying signals through interaction of two or more enzymes, such as RNA nucleases, proteases, peptidases, lipases, glycases, and endonucleases, etc. These devices and methods may be used to assay a wide variety of samples and target nucleic acid sources, for the presence or absence of a specific target nucleic acid sequences. Compositions and kits, useful in practicing these methods, for example detecting a target nucleic acid sequence in a biological sample, are also described.

In an embodiment, a device may aid in determining a presence of a target nucleic acid sequence of dsDNA (double stranded DNA) or ssDNA (single-stranded DNA). The device includes an assay area including at least one reporter molecule, a tether molecule, and a solid support. The tether molecule includes a first end, a second end, and at least one indicator nucleic acid sequence for sensing the presence of an activated Cas 12 and/or Cas12a endonuclease (DNase), wherein the at least one reporter molecule is attached at the first end, and the solid support is attached at the second end.

The disclosed device further includes a detection area, and a filter positioned between the detection area and the assay area.

In an embodiment, a method of constructing a device includes synthesizing a tether molecule having a first end, a second end, and at least one indicator nucleic acid (DNA) sequence positioned between the first and second end, the at least one indicator nucleic acid sequence. In an embodiment, the indicator sequence may include at least two nucleobases, including two thymine or adenosine bases. The method further includes attaching a reporter molecule at the first end of the tether molecule, and attaching the second end of the tether molecule to a solid support, wherein the solid support is a nanoparticle. In an embodiment, the solid support has at least one measurable dimension of at least about 1.0 nm.

In an embodiment, a system for determining a presence of a target nucleic acid sequence may include a modified Cas12a molecule, including a guide RNA sequence complementary to the target nucleic acid sequence, a device for determining a presence of a nuclease, the device including at least one reporter molecule, a solid support, and a tether molecule having a first end, a second end, and at least one indicator nucleic acid sequence positioned between the first and second end, wherein the at least one reporter molecule is attached at the first end, and the solid support is attached at the second end of the tether molecule. The device further includes an assay compartment, a detection compartment; and a filter positioned between the assay compartment and the detection compartment, wherein the filter is permeable to an untethered reporter molecule.

In an embodiment, a method of detecting a target nucleic acid sequence in a biological sample may include combining the biological sample with a composition to create a sample mixture, the composition including at least one modified Cas molecule including a guide RNA having a sequence complementary to the target nucleic acid sequence. The method further includes incubating the sample mixture with an indicator device to create an assay mixture, the indicator device including a solid support, at least one reporter molecule, and a tether molecule having a first end and a second end, wherein the tether molecule is attached at a first end to the solid support and attached at the second end to the at least one reporter molecule, the tether molecule including at least one indicator nucleic acid sequence positioned between the first and second ends. The method further includes incubating the assay mixture for an assay period, a step of applying a separating force to the assay mixture, and a step of detecting a signal from an untethered reporter molecule, wherein if the detected signal is greater than a background value, the target nucleic acid sequence is present in the biological sample, wherein the background value is obtained from a biological sample lacking the target nucleic acid sequence. In an embodiment the biological sample may be combined with a composition comprising at least one Cas molecule modified with a guide RNA sequence, wherein the guide RNA sequence is complementary to the target nucleic acid sequence, the solid support may be a SEPHACRYL® (cross-linked copolymer of allyl dextran and N,N'-methylene bisacrylamide) bead, the reporter molecule may be a luciferase enzyme, and centrifugation may be used to separate tethered from untethered luciferase enzymes, which may pass through a filter into the detection area containing luciferin.

An embodiment of the disclosed method may be useful in identifying pathogens in a sample obtained from a human or non-human patient, from an environmental sample, an agricultural sample, or a food sample. An embodiment of the disclosed method may be useful in identifying exogenous DNA or RNA, for example microRNA (miRNA) species.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 3A depicts an embodiment having a first device for detecting the presence of an activated Cas protein, with a reporter molecule tethered to the first device. FIG. 3B depicts an embodiment having a first device for detecting the presence of an activated Cas protein, wherein the reporter molecule is an enzyme, here a nuclease, that targets an indicator sequence on a second device, wherein the second device has a second reporter molecule.

DEFINITIONS

Figure 1:
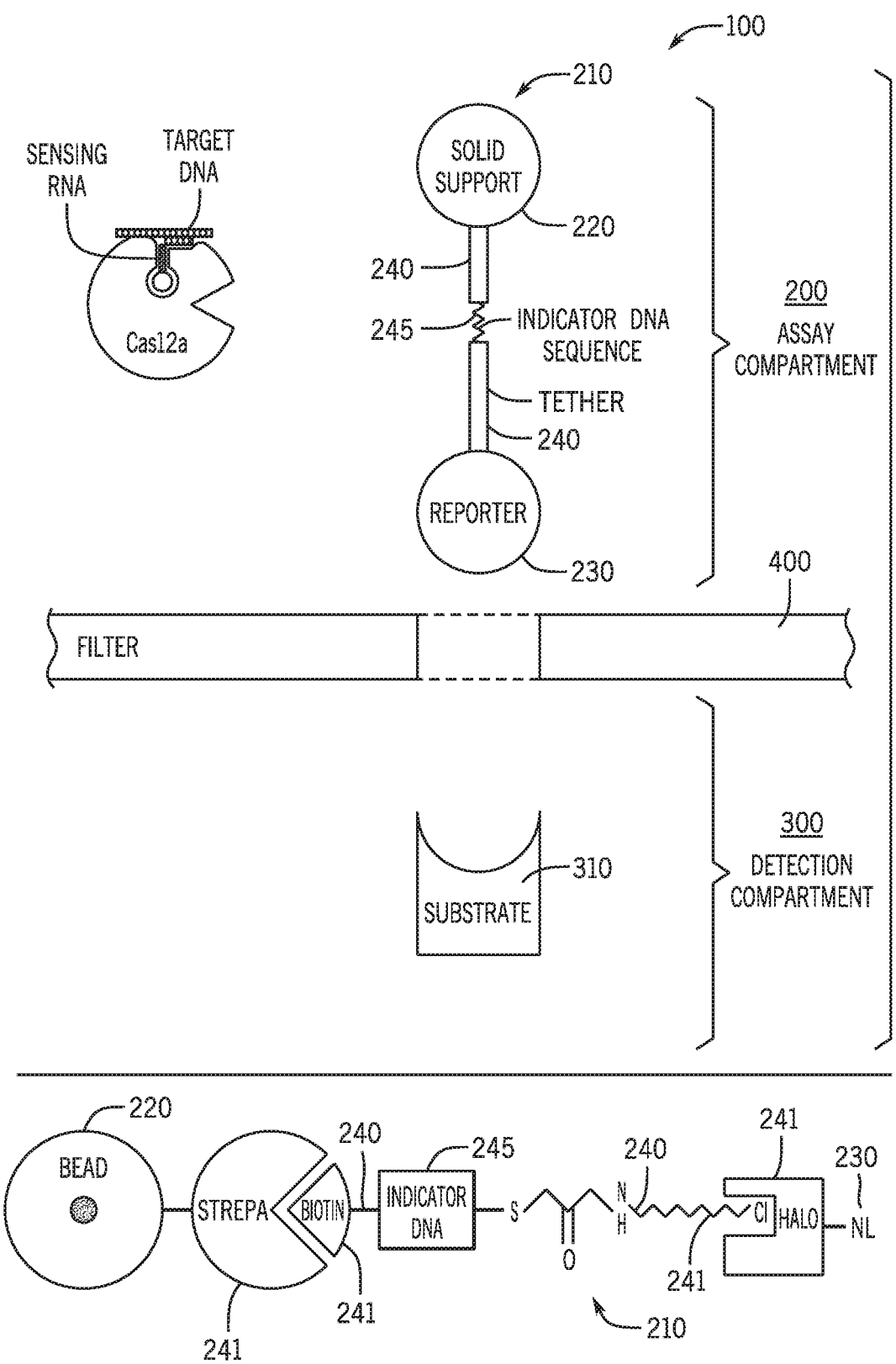
FIG. 1 is a schematic of an embodiment of the presently disclosed devices. The upper panel shows a tethered reporter molecule separated from a detection compartment by a filter or membrane permeable to the untethered reporter molecule. The lower panel is a detailed schematic showing construction of an embodiment of the tethered reporter molecule.

"Oligonucleotide," "polynucleotide," and "nucleic acid," are used interchangeably herein. These terms may refer to a polymeric form of nucleic acids of any length, strandedness (double or single), and either ribonucleotides (RNA) or deoxyribonucleotides (DNA), and hybrid molecules (comprising DNA and RNA). The disclosed nucleic acids may also include naturally occurring and synthetic or non-natural nucleobases. Natural nucleobases include adenine (A), thymine (T), cytosine (C), guanine (G), and uracil (U).

"Complementarity" refers to a first nucleic acid having a first sequence that allows it to "base pair," "bind," "anneal", or "hybridize," to a second nucleic acid. In an embodiment, the first nucleic acid may be an RNA sequence and the second may be a single- or double stranded DNA or RNA sequence. In an embodiment, the first nucleic acid may be a DNA sequence and the second may be a single- or double-stranded DNA or RNA sequence. Binding may be affected by the amount of complementarity and certain external conditions such as ionic strength of the environment, temperature, etc. Base-pairing rules are well known in the art (A pairs with T in DNA, and with U in RNA; and G pairs with C). In some cases, RNA may include pairings where G may pair with U. Complementarity does not, in all cases, indicate complete or 100% complementarity. For example, complementarity may be less than 100% and more than about 60%, for example two sequences may be greater than 60% or less than 100% complementary over a given length of sequence (for example greater than 10 nt. and less than about 220 nt).

"Protein," "peptide," "polypeptide" are used interchangeably. The terms refer to a polymeric form of amino acids of any length, which may include natural and non-natural residues. The residues may also be modified prior to, or after incorporation into the polypeptide. In some embodiments, the polypeptides may be branched as well as linear.

"Programmed," in reference to Cas proteins, refers to a Cas protein that includes a guide RNA that contains a sequence complementary to an activator (or target) sequence. Typically, a programmed Cas protein includes an engineered guide RNA.

"Cas protein" is a CRISPR associated protein. The presently disclosed Cas proteins possess a nuclease activity that may be activated upon binding of a target sequence to a guide RNA bound by the Cas protein. As disclosed in more detail below, the guide RNA may, with other sequences, comprise a crRNA, which may, in some embodiments, be processed from a pre-crRNA sequence. In an embodiment, the guide RNA sequence may include natural or synthetic nucleic acids, for example modified nucleic acids such as, without limitation, locked nucleic acids (LNA), 2'-o-methylated bases, or even ssDNA (single stranded DNA). In many embodiments, the disclosed Cas proteins are selected from the Cas12 group, which may be derived from various sources known to those of skill in the art.

"Coding sequences" are DNA sequences that encode polypeptide sequences or RNA sequences, for example guide RNAs. Coding sequences that encode polypeptides are first transcribed into RNA, which, in-turn, may encode the amino acid sequence of the polypeptide. Some RNA sequences, such as guide RNAs may not encode amino acid sequences.

"Native," "naturally-occurring," "unmodified" or "wild-type" describe, among other things, proteins, amino acids, cells, nucleobases, nucleic acids, polynucleotides, and organisms as found in nature. For example, a nucleic acid sequence that is identical to that found in nature, and that has not been modified by man is a native sequence.

"Recombinant," "engineered," and "modified" as used herein, means that a particular nucleic acid (DNA or RNA) is the product of human intervention, and is not generally found "in nature." Specifically, the particular sequence has been isolated and/or modified by one or more of in-vitro synthesis, mutation, deletion, substitution, cloning, cleavage, ligation, and amplification.

"Label" or "labelling" refers to a component with molecule that renders the component identifiable by one or more techniques.

The following disclosure is understood not to be limited to particular embodiments described below. Moreover, the provided terminology is not meant to be limiting.

DETAILED DESCRIPTION

Embodiments disclosed herein include devices, compositions, methods, and systems for detecting the presence or absence of specific target nucleic acid sequence (e.g. double-stranded DNA sequences) in a sample. In an embodiment, the devices, compositions, methods, and systems may be useful in rapid, sensitive, and cost-effectively diagnosing a patient or sample having a viral, bacterial, parasitic, or fungal infection, or a condition, disease, or disorder that may be identified by the presence of one or more specific nucleic acid sequences. In an embodiment, the disclosed devices, compositions, methods, and systems may be useful in genetic screening, cancer screening, mutational analysis, single nucleotide polymorphism analysis, etc.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Clustered regulatory interspaced short palindromic repeats (CRISPR) were discovered in the late 1980s. While the notion that these sequences are involved in bacterial defense systems was suggested over the subsequent decades, it was not until the mid to late 2000s that it became more widely accepted. During that time several papers elucidated the basics of this acquired immunity system: foreign DNA sequences (e.g. from plasmids and viruses) flanked by palindromic repeats are incorporated in into the host genome, and their RNA products direct Cas complexes to cut nucleic acids containing complementary sequences.

Simplified complexes of CRISPR-associated (Cas) proteins in combination with engineered guide RNAs were shown to be able to locate and cleave specific DNA sequences. This lead to an explosion of novel technologies, especially genome editing. Further research has shown that these proteins may be used to edit genomes in vivo. CRISPR systems are found in archaea and a number of bacteria. In addition to their more widely recognized ability to target DNA, some types of Cas proteins also have indiscriminant nuclease activity. For example, the Cas12a protein has single-stranded and double-stranded endonuclease activity.

Endonuclease (DNase) enzymes cleave polymeric deoxyribonucleic acids (DNA) to produce nucleotides or shorter polynucleotides. Most DNases are known to target double-stranded DNA, while some DNases target single-stranded DNA. Cas12a belongs to the type V CRISPR system, and possesses single-stranded and double-stranded DNase activity. Specifically, Cas12a is activated when it binds to a target-DNA (or activator-DNA) using its guide RNA. In an embodiment, the target or activator DNA may be a complementary single-stranded sequence or double-stranded sequence.

Cas12a (Cpf1) is therefore a CRISPR DNase with both sequence specific and non-specific nuclease activity. Like other Cas proteins, Cas12a is "programmed" upon binding a guide RNA sequence. Cas12a is activated by binding either single-stranded or double-stranded DNA, and has the ability to cleave double-stranded DNA at targeted and non-targeted sequences. Cas12 also possesses indiscriminate single-stranded DNase activity. The enzymatic activity associated with non-specific (indiscriminant) DNase activity appears to be much higher than the targeted activity.

Like several other CRISPR proteins, Cas12a's guide RNA sequence may be modified, or "programmed," to recognize and bind specific target nucleic acid sequences. This type of "programming" renders the protein's collateral cleavage function specific for a given target DNA sequence. In nature, this may be a foreign or viral sequence, but when engineered in-vitro, the target sequence can be selected from any single or double-stranded sequence complementary to the engineered portion of the guide RNA.

Embodiments disclosed herein include devices, compositions, methods, and systems for detecting the presence or absence of specific single-stranded or double-stranded target DNA sequences. In some embodiments, such as that depicted in FIG. 1, the disclosed device 100 includes an indicator device 210 that further includes a reporter molecule 230 connected to a solid support 220 via a tether molecule 240 having at least one indicator sequence 245. In some embodiments, the device 100 may further include a filter 400 or membrane that is permeable to the untethered reporter molecule. A detection compartment 300 or area may allow for a separate area for detection of untethered reporter molecules away from the tethered reporter molecules in the assay compartment 200. The detection area 300 may also include one or more molecules 310, such as substrates or binding proteins for interacting with untethered reporter molecules. The lower portion of FIG. 1 shows an embodiment of an indicator device 210 that includes a reporter 230, tether 240, and solid support 220. In this embodiment, the reporter 230 is luciferase (here Nanoluc® (Promega), designated "NL"), which is fused to a Halotag® (Promega, HT). The HaloTag protein is covalently bound to a chlorinated tag ligand, which in turn is covalently attached, via a sulfur and succinimide group to the indicator sequence 245 at a proximal end. At the distal end of the indicator sequence, is a covalently attached biotin molecule, which in turn is bound by a streptavidin protein covalently attached to a bead. In an embodiment, the HT, chlorinated tag, biotin, and streptavidin may be referred to as anchor molecules 241.

Kits useful for detecting a target DNA in a sample are also disclosed, wherein the kit includes at least one Cas12a protein (also shown in FIG. 1) that may also include a guide RNA sequence, and in another embodiment a guide RNA sequence+an activator DNA sequence. The at least one Cas12a may be in the form of a coding sequence and the kit may further include one or more guide RNAs (or sequences coding same) for programming the Cas12a proteins, that is the Cas12a protein includes a guide RNA sequence. In some embodiments, kits may include tethered reporter molecules, solid supports, and substrates or capturing molecules for interacting with the reporter molecules.

The disclosed system provides for inexpensive and rapid detection of nucleic acid target sequences from a variety of sources comprising single or double-stranded DNA, including, without limitation mammals, viruses, bacteria, fungi, etc. the disclosed devices, systems, and methods provide for minimal sample preparation, and, in an embodiment, without the need to amplify nucleic acids from the sample. The samples may be biological samples from a human or non-human patient, or an environmental sample from water, food, etc. In some embodiments, the disclosed compositions, devices, and systems may include a reporter molecule such as a fluorophore, or an enzyme, for example a phosphatase or luciferase (as described above). In some embodiments, the luciferase may be Nanoluc® (Promega) and the phosphatase may be alkaline phosphatase. This may allow for methods of detecting target nucleic acid sequences using fluorometric, luminescent, and/or colorimetric assays. In other embodiments, the reporter molecule may be a nanoparticle, for example a metal nanoparticle such as a gold nanoparticle.

Figure 2:
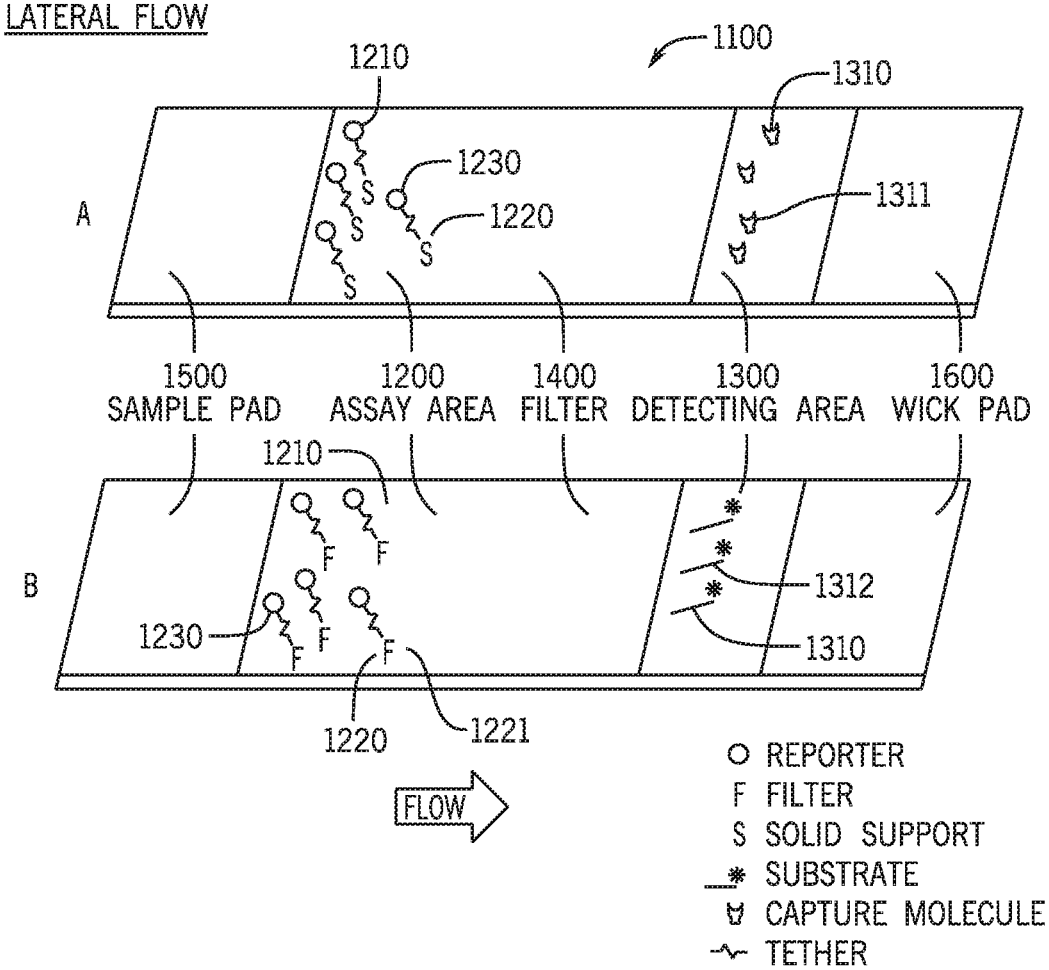
FIG. 2 shows various embodiments of detection devices for use with any of the disclosed methods and systems. Panels A and B show lateral flow embodiments with arrow showing direction of flow. Panels C and D show microfuge tube embodiments.
Figure 2:
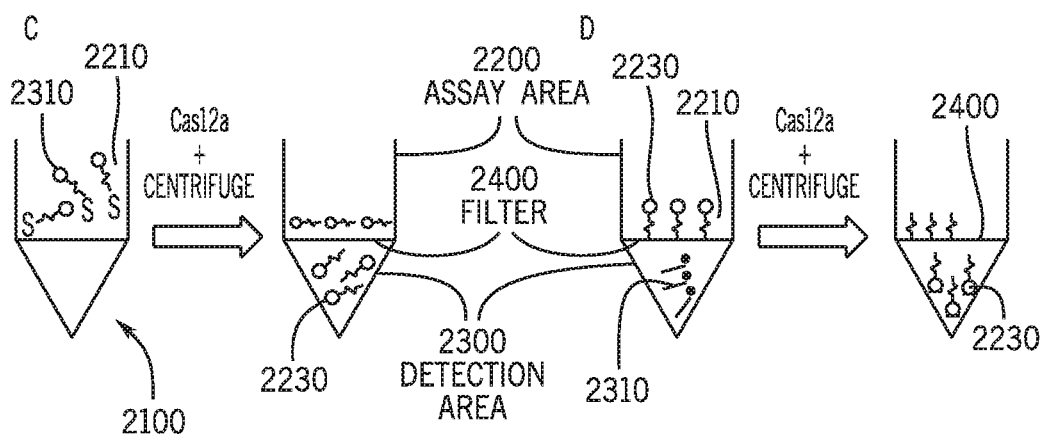

As shown at FIG. 2, detection devices useful for identifying the presence of a target DNA may include lateral flow 1100 (Panels A and B) or chambered microfuge tubes 2100 (Panels C and D). In some embodiments, the chambered microfuge tubes 2100 may have a removable assay area 2200 that includes the filter 2400. The lateral flow-based device 1100 may include a sample pad 1500, an assay area 1200, a detection area 1300, and a wick pad 1600 for helping to draw fluid from the sample pad 1500. In these embodiments the reporter molecule 1230 may be tethered to a solid support 1220 to create an indicator device 1210 at the assay area 1200, which may further include a filter 1400. In some embodiments, such as shown in the upper panel of FIG. 2, the filter 1400 may also be the solid support 1221 (Panel B) and the reporter 1230 may be tethered to the filter 1400 or 1221. The detection area may include a molecule 1310 with a capture surface 1311 for capturing the reporter (Panel A), or a substrate 1312 for interacting with the reporter (Panel B). The microfuge-based embodiments shown in the lower portion of FIG. 2 (Panels C and D) may be used with methods that use centrifugation to separate tethered from untethered reporter molecules. Here again, the filter 2400, prevents tethered reporter molecules 2310 on the indicator device 2210 from entering the detection area 2300 and allows untethered reporter molecules 2230 to enter the detection area 2300 (Panel C). Likewise, Panel D shows reporter molecules 2230 and tethers 2210 attached directly to the filter 2400 (Panel D), allowing untethered molecules to interact with the substrate 2310.

Figure 3A:
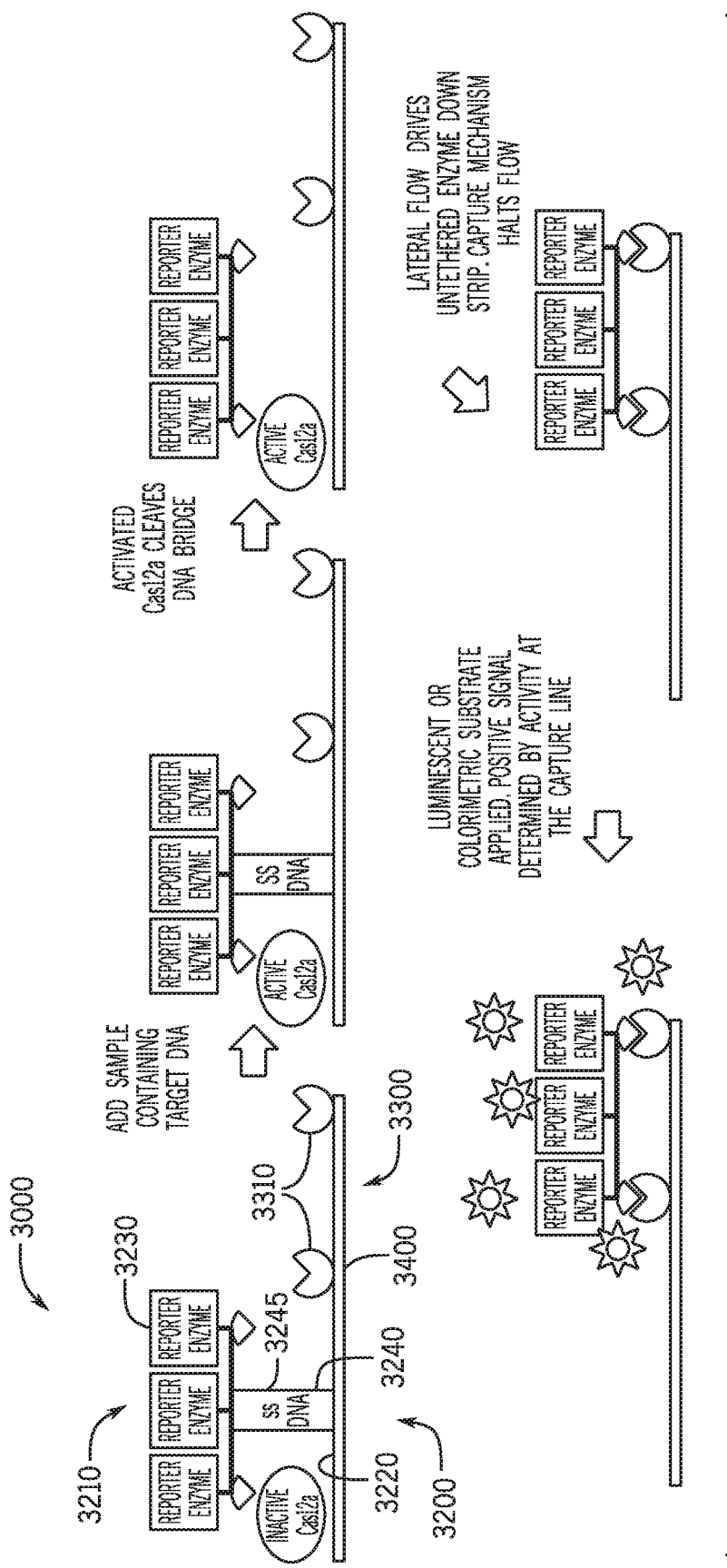
FIGS. 3A and 3B are diagrams showing embodiments of the disclosed device and method.

Other embodiments may include microfluidic devices, and/or may combine aspects of the devices shown in FIG. 2. For example, shown in FIG. 3 is a device 3000 with an assay area 3200 and a detection area 3300 comprising a capture molecule 3310, wherein the reporter molecule 3230 on the indicator device 3210 is an enzyme (here luciferase) tethered to the filter 3400 (via a tether 3245, here ssDNA 3240), which is also the solid support 3220. In some embodiments, combining capture of a reporter molecule with enzymatic activity may aid in enhancing and concentrating signaling. The disclosed devices, when combined with visual inspection, Raman detection, Plasmon resonance, or other detection methods may sensitively and accurately identify the presence of target DNA sequences in a sample. In some embodiments, the devices and methods may be useful for processing a plurality of samples simultaneously and rapidly. In addition, the disclosed methods and devices may provide for rapid and simultaneous detection of different target sequences in the same or different samples.

Figure 3B:
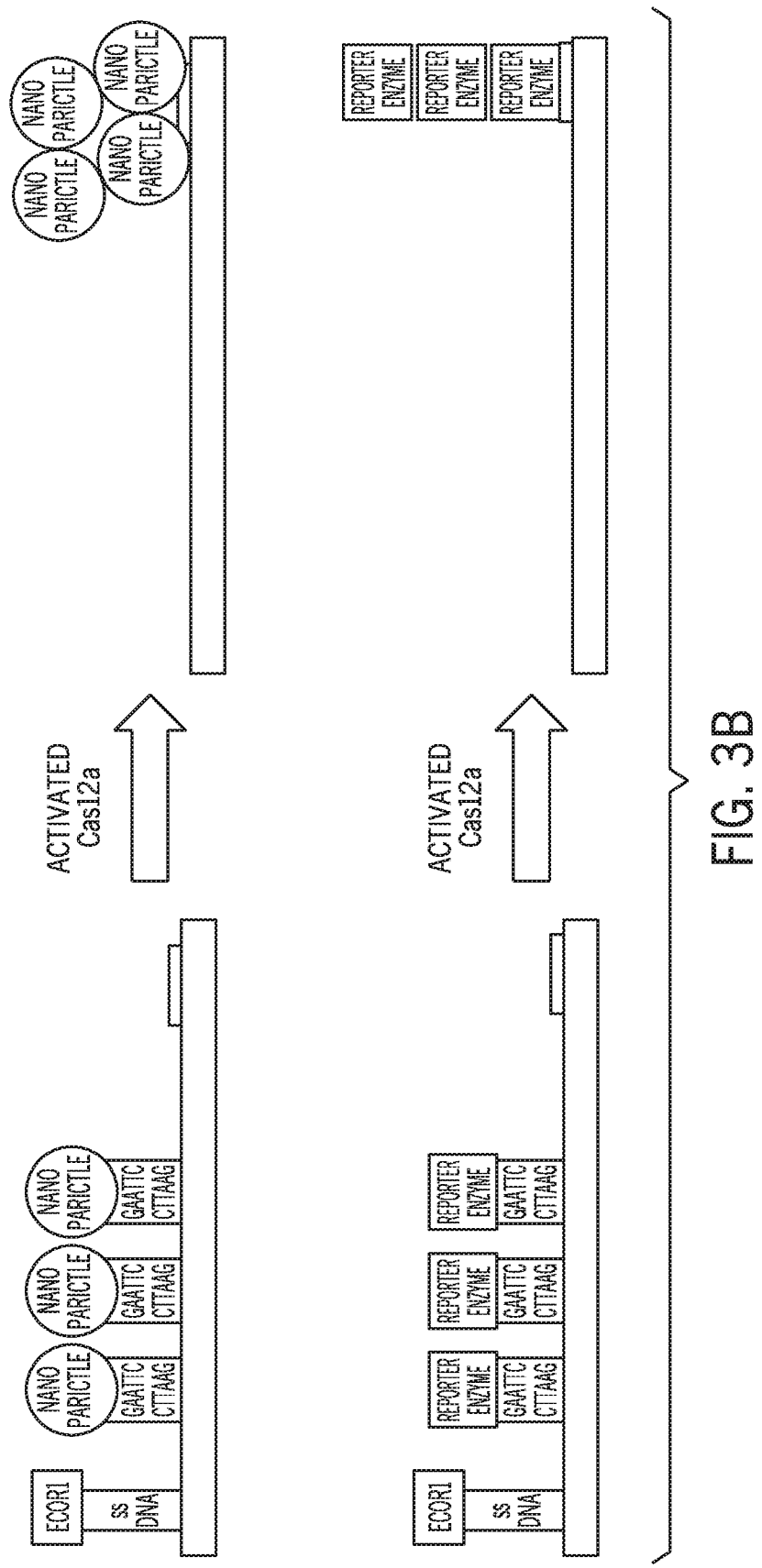

FIG. 3B depicts two embodiments of the presently disclosed device, having a first indicator device and a second indicator device. In the upper panel, the first indicator device includes a first indicator sequence that may cleaved by a Cas protein, and a first reporter molecule that is a restriction endonuclease (here EcoRI). The second indicator device, which may be proximal or distal the first indicator device (e.g. downstream) includes a second indicator sequence that is cleavable by the first reporter molecule. In these embodiments, the second indicator sequence is a double-stranded DNA sequence with a target sequence for the restriction endonuclease that may differ from the sequence recognized by the Cas protein. The second reporter device may be a nanoparticle or an enzyme that may produce a detectable signal (e.g. luciferase).

The embodiments depicted in FIG. 3B may provide for signal amplification and/or reduction of background. In an embodiment, as described below the first reporter molecule may be an enzyme such as a peptidase, protease, glycase, lipase, endonuclease, etc. In some embodiments the first reporter molecule may be Cas protein that is different that may cleave the second indicator sequence but not the first indicator sequence. In some embodiments, the number of second indicator devices may be greater than the number of first indicator devices. In some embodiments, the ratio of first indicator device to second indicator device is 1:1, 1:2, 1:3, 1:4, 1:5, 1:6, 1:7, 1:8, 1:9, 1:10, 1:20, 1:50, or 1:100.

Device for Detecting a Single- or Double-Stranded Target DNA Sequence

Embodiments disclosed herein include indicator devices for the detection of a target nucleic acid sequences. In some embodiments, the disclosed device will include a reporter molecule, a solid support, and a tether molecule positioned between the reporter molecule and solid support. The tether molecule connects, directly or indirectly, the reporter molecule to the solid support. In some embodiments, the device may further include a filter that may help to separate the solid support from an untethered reporter molecule. In some embodiments, the filter may be permeable to an untethered reporter molecule, but not a tethered reporter molecule.

The tether or bridge molecule includes at least one "indicator" sequence. The indicator sequence may be susceptible to cleavage by a nuclease. In an embodiment, the nuclease is a Cas protein, for example an activated Cas12a DNase. In an embodiment wherein the indicator sequence is single-stranded DNA, the indicator sequence may include at least two thymine residues. The indicator sequence may be between 2 nucleotides and 50 nucleotides, or more, in length. The tether may include two or more indicator sequences of the same or different sequence. In some embodiments, the indicator sequence may be connected to a non-nucleic acid molecule at its 5' and/or 3' ends, or positioned between two or more indicator sequences. In some embodiments, the indicator sequence may include a thiol or biotin at the 5' and/or 3' end. In some preferred embodiments, the sequence of the indicator sequence is 5'-TTATT-3', or TTATTTTATT (SEQ ID NO: 1).

In an embodiment, the indicator sequence may be other than nucleic acid. For example, the indicator may be a lipid, carbohydrate, protein, peptide, or other sequence that may be cleaved by an enzyme. In an embodiment, the indicator sequence may be susceptible to cleavage by one or more of SUMO, TEV protease, lipase, glycase, etc.

The disclosed devices may include indicator devices with one or more indicator sequence types. For example, the device may include a first indicator device having a nucleic acid indicator sequence that may be cleaved by an activated Cas protein, and a second indicator sequence that may be cleaved by a protease. In this embodiment, the first indicator device may include a reporter molecule that is a protease, and the second may include a reporter molecule that is detectable by one or more detection methods (for example the reporter molecule on the second indicator device may be luciferase).

Where the tether includes a single-stranded DNA indicator sequence and one or more non-DNA molecules, in addition to the indicator sequence, the non-DNA sequences may be one or more of double-stranded RNA, double-stranded DNA, and/or single-stranded RNA. In an embodiment, the tether molecule may include one or more of single-stranded RNA, single-stranded DNA, double-stranded DNA, ribonucleotides, deoxyribonucleotides, lipids, peptides, carbohydrates, polyethylene glycol (PEG), "click" chemistry tags, biotin, streptavidin, DNA, maleimide, sulfur, thiol, amino acids, proteins, peptides, succinimide, bacterial proteins, synthetic proteins, haloalkane dehalogenase (HaloTag), chloroalkane, triazol, sulfone, heterocyclic or carbocyclic small molecules, aliphatic or heteroaliphatic small molecules, inorganic species, organometallic species, radioactive molecules and combinations thereof.

The tether molecule may include at least one anchor domain, sequence, residue, or structure at a first end and/or at a second end. The anchor domains may aid in contacting and attaching the tether to the reporter molecule (reporter anchor) or solid support (support anchor). In some embodiments, the anchor may be covalently or non-covalently bonded to the tether, reporter molecule, and/or solid support. Those embodiments having a non-covalent bond, the bond may be sufficiently strong to reduce disassociation in most physiologic environments. In other embodiments, the tether may be covalently attached directly to the reporter molecule and/or the solid support. FIG. 1 depicted the anchor structures such as halo tag ligand, and biotin.

Reporter Molecule

The reporter molecule may be tethered to a solid support by the indicator sequence. In an embodiment, the reporter molecule may be easily detected when separated from the solid support, or may cleave an indicator sequence tethered to a second reporter molecule. In some embodiments, the reporter molecule is selected from one or more of a protease, peptidase, lipase, glycase, nuclease, endonuclease, restriction endonuclease, Cas protein, fluorophore, fluorescent molecule, luminescent molecule, a protein, a fusion protein, an enzyme, a SERS (surface enhanced Raman spectroscopy) particle, a heterocyclic or carbocyclic small molecule, an aliphatic or heteroaliphatic small molecule, an inorganic species, organometallic species, radioactive molecule, a nanoparticle and combinations thereof. In some embodiments, two or more reporter molecules of the same or different type are connected to a tether or solid support. As an example, the tether may be connected to a luciferase enzyme and a nanoparticle, or the tether may be connected to two or more luciferase molecules. In some preferred embodiments, the reporter molecule may be one or more of a fluorophore, NanoLuc, firefly luciferase, *Renilla reniformis* luciferase, alkaline phosphatase, horseradish peroxidase, beta galactosidase, glucose oxidase, α- or β-amylase, fluorescent protein, green fluorescent protein, yellow fluorescent protein, beta-glucuronidase, fluorescein dyes, alexafluors, quantum dots, quantum nanodots, metal, and gold.

The reporter molecule may be detected directly or indirectly by various methods. For example, where the reporter molecule is a fluorophore, for example A488, the untethered fluorophore may be detected by exciting it at a given wavelength of light and detecting an emission wavelength. In an embodiment, the untethered fluorophore signal may be compared to the signal produced by the fluorophore remaining tethered, or the untethered signal may be compared with a standard. Where the reporter is an enzyme, for example luciferase, the presence of the untethered enzyme may be detected by interaction with a substrate, such as luciferin. In an embodiment, the reporter molecule may be a cleavage enzyme that may untether a second reporter molecule on a second indicator device by cleaving a second indicator sequence. In these embodiments, the second indicator device may be located in, near, or distal to a first indicator device with the cleavage enzyme. In some embodiments, wherein the reporter molecule is a detectable molecule or enzyme, the substrate may be located away from or distal to the solid support, such that the enzyme will not contact the substrate until it is untethered from the solid support. In other embodiments, the reporter molecule may be detected directly, for example where the reporter molecule is a nanoparticle, such as a SERS particle. In these embodiments, the particle may interact with a molecule that has affinity for, captures, recognizes, and/or binds to the reporter molecule. For example, the reporter molecule may be a nanoparticle that, when untethered from the solid support may be translocated to a site away from the solid support and be captured, for example by an antibody, binding protein, or magnetic structure designed to interact with the reporter molecule.

In an embodiment, the reporter molecule untethered from the solid support may be attracted to or captured by another molecule. In some embodiments, an untethered reporter may be concentrated to help enhance detection.

A tethered reporter molecule is connected to a tether with all indicator sequences intact, uncleaved, and attached to a solid support. The reporter molecule may produce a signal, which may be detected in a variety of ways, or may cleave a second indicator sequence at a second indicator device. In some embodiments, wherein the reporter molecule produces, directly or indirectly, a signal, the signal is one or more of luminescence, fluorescence, plasmonic resonance, turbidity, absorbance, or electrochemical.

Solid Support

The solid support may be various structures or substances, for example at least one of a surface, fiber, bead, or particle. The solid support may include of one or more of glass, metal, polymer, cellulose, SEPHACRYL®, agarose, acrylamide, or dextran. In some embodiments, a plurality of tether molecules may attach to a solid support. In other embodiments, a single solid support molecule may attach to a single tether. In some embodiments, the solid support is or includes a filter, mesh, fabric or other material that is permeable to an untethered reporter molecule but may be impermeable to tethered reporter molecules. That is, in these embodiments, when untethered, a reporter molecule may flow through, exit, be expelled, or otherwise pass by or through the solid support to relocate to a detection area, and be detected or to produce a signal that is detected. In some preferable embodiments, the solid support may be a magnetic bead or a cellulose binding protein.

In an embodiment, the solid support may be a pad or filter of a lateral flow device. In these embodiments, the reporter may be attached to a tether that is in turn attached to the pad or filter of the lateral flow device. When an indicator sequence of the tether is cleaved, the untethered reporter may flow through or over the pad or filter toward a detection area. In these embodiments, the untethered reporter may be translocated away from the cleaved tether and solid support by capillary action.

Cas Protein

The disclosed Cas proteins may be derived from various sources including archaea and bacteria. In some embodiments, a native Cas protein may be derived from *Paludibacter, Carnobacterium, Listeria, Herbinix, Rhodobacter, Leptotrichia, Lachnospiraceae, Eubacterium,* or *Clostridium*. In some embodiments, the native Cas protein may be derived from *Paludibacter propionicigenes, Carnobacterium gallinarum, Listeria seeligeri, Listeria newyorkensis, Herbinix hemicellulosilytica, Rhodobacter capsulatus, Leptotrichia wadei, Leptotrichia buccalis, Leptotrichia shahii, Lachnospiraceae bacterium* NK4A179, *Lachnospiraceae bacterium* MA2020, *Eubacterium rectale, Lachnospiraceae bacterium* NK4A144, and *Clostridium aminophilum*.

The presently disclosed Cas protein is homologous to a native Cas protein. In some embodiments, the disclosed Cas protein is greater than 75%, 80%, 85%, 90%, 95%, 97%, 98%, or 99%, and less than about 100%, 99%, 98%, 97%, 95%, 90%, 85%, 80%, or 75% identical to a native Cas protein sequence. The disclosed Cas protein may have one or more HEPN domains, and may be able, after activation, to cleave single stranded RNA, including precursor guide RNA and indicator RNA.

Activation of a Cas protein may include contacting one or more target sequences with a guide RNA sequence associated with the Cas protein. In some embodiments, the guide RNA of the Cas protein may help to activate the Cas protein's nuclease activity by hybridizing to a complementary single- or double-stranded target sequence.

The disclosed Cas proteins may be Cas 12 proteins. In an embodiment, the Cas protein is a modified Cas12 protein that is modified, or engineered or mutated, to alter its interaction with guide or target sequences and/or to alter its nuclease activity, for example specificity, turn-over, nucleotide preferences, etc. In other embodiments, the Cas protein may be fused to another protein, peptide, or marker to aid in isolation, identification, separation, nuclease activity, target sequence binding, etc.

Guide RNA Sequence

Guide RNAs include at least one sequence complementary to a target sequence. In some embodiments, this target-complementary sequence may be referred to as a spacer sequence, additional sequences may be referred to as scaffold sequences. In some embodiments, the spacer sequence is derived from a human (e.g. genomic DNA or transcribed RNA) or non-human source (for example a pathogen). In some embodiments, the pathogen selected may be from bacteria, viruses, fungi, and parasites. In some embodiments the pathogen may be a bacterium selected from *Mycobacterium, Streptococcus, Pseudomonas, Shigella, Campylobacter, Salmonella, Clostridium, Corynebacterium,* and *Treponema*. In some embodiments the virus may be selected from DNA or RNA viruses including Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. In some embodiments, pathogenic fungi include *Candida, Aspergillus, Cryptococcus, Histoplasma, Pneumosystis,* and *Stachybotrys*.

In other embodiments, the spacer RNA sequence is complementary to a non-pathogen. For example, the spacer RNA sequence may be engineered to hybridize to any nucleic acid sequence of interest. In some embodiments, the guide RNA sequence may be engineered to be complementary to a mammalian sequence of interest, for example a genomic sequence, or transcribed sequence (mRNA, microRNA, etc.). In various embodiments, the guide RNA may include a sequence complementary to a sequence associated with a mammalian condition, disease, or disorder, such as cancer, viral infection, bacterial infection, fungal infection. In some embodiments, the guide RNAs may be complementary to an mRNA or micro RNA, for example a microRNA sequence in a microRNA signature. In some embodiments, the guide RNA sequence may be within a precursor RNA, which may, in turn be part of an array with a plurality of guide RNA sequences. In some embodiments, precursor RNA sequences may be processed by the Cas protein to provide guide RNA sequences.

Guide RNA sequences include the spacer sequence, which is complementary to the target sequence, and a more constant sequence that is 5' of the spacer sequence. This constant sequence may be referred to as a scaffold sequence, repeat, handle, or constant region and aids in binding the guide RNA to the Cas protein. In some embodiments, the constant sequence can be replaced with that of an evolutionarily related constant sequence. As is known in the art, Cas proteins may be grouped into different families comprising functional groups that recognize orthogonal sets of crRNAs and possess different nucleotide cleavage specificity. In some embodiments, the constant sequence can be modified to improve affinity and stability by including naturally occurring and synthetic or non-natural nucleobases or backbone modifications. In some embodiments, the constant sequence may include a precursor sequence. In an embodiment, a pre-crRNA sequence may be processed to form a crRNA sequence, which includes the guide sequence.

A Cas protein comprising a guide RNA may be referred to as a "programed" Cas protein. Guide RNA sequences may be introduced to and bound by a Cas protein. For example, the guide RNA may contact the Cas protein in a cell or outside a cell. Various methods may be used to contact the guide RNA with the Cas protein to produce a programmed Cas protein. In some embodiments, contacting requires less than about 2 hours, for example less than about 90 min., 60 min., 40 min., 30 min., 20 min., 10 min., 5 min., 4 min., 3 min., 2 min, or 1 min.

Target/Activator Sequences

Target nucleic acid sequences may be identified from various sources, including, without limitation, plants, mammals, parasites, amoebae, viruses, bacteria, and fungi. In some embodiments, the target or activator sequence is a microbial or viral sequence, in still other embodiments the target sequence is a mammalian genomic or transcribed sequence. In some embodiments, the source may be a human, non-human, or animal. In some embodiments, an animal source may be a domesticated or non-domestic animal, for example wild game. In some embodiments, the domesticated animal is a service or companion animal (e.g. a dog, cat, bird, fish, or reptile), or a domesticated farm animal.

For target sequences from pathogenic sources, the pathogen may have significant public health relevance, such as a bacteria, fungus, or protozoan, and the target sequence may be found, without limitation, in one or more of *Clamydia trachomatis*, *Neisseria gonorrhoeae*, *Trichomonas vaginalis*, *Ureaplasma* species, *Plasmodium falciparum*, *Plasmodium vivax*, *Mycobacterium ulcerans*, *Eschericia coli* 0157: H7; Hepatitis B; human papillomavirus; influenza A, B, C, or D virus; human immunodeficiency virus; or herpesviruses.

Assay Area

Embodiments of the disclosed devices may include an assay area. In an embodiment, the assay area may include at least one first indicator device comprising a first indicator sequence to tether a reporter molecule to a solid support. In some embodiments, the solid support may be a filter or membrane that may allow translocation untethered reporter molecules.

The Assay area may include a first indicator device having a first indicator sequence, and a second indicator device having a second indictor sequence.

Detection Area

Embodiments of the disclosed devices include a detection area for capturing, identifying, or detecting the presence of an untethered reporter molecule. In some embodiments, the detection area is free of tethered reporter molecules, and separate from and distal to the solid support. For example, in embodiments where the device is part of a lateral flow device, the detection area may be a test line or control line, and distal to a sample pad or a filter that includes the solid support tethered to the reporter molecule.

The detection area may include a substrate for interacting with an untethered reporter molecule. For example, in these embodiments, the device may be separated from the detection area by a filter, membrane, gel, hydrogel, or polymer that may be permeable to an untethered reporter. In these embodiments, application of a force (for example centrifugation, electromagnetic field, fluid flow, or combination thereof) may help transport the untethered reporter molecule across or through the filter/membrane, and into the detection area. In some of these embodiments, the untethered reporter molecule may bind to the substrate and produce a signal, which may be detected by a detection device. In these embodiments, the solid support may be unable to move across or through the filter or membrane, and therefore may help prevent reporter molecules that remain tethered to the solid support from entering the detection area.

The detection area may include a protein or molecule that may capture or bind the reporter molecule. In these embodiments, the capture molecule may aid in transporting, localizing, fixing, and/or concentrating the untethered reporter molecules. This may, in turn, aid in enhancing a signal from the reporter molecule and therefore increase sensitivity of an assay for detecting untethered reporter molecules. In some of these embodiment, the capture molecule may be a protein with affinity for the reporter molecule, such as an antibody or monobody. In these embodiments, the reporter molecule may be modified to include a tag that may be bound by the antibody. In other embodiments, the capture molecule may be a magnetic particle that may interact, magnetically, with the reporter molecule.

Methods

Methods disclosed herein include methods of making the disclosed devices and methods of using same to detect a target sequence in a sample. The disclosed methods may be useful in detecting a target nucleic acid sequence in a sample, for example a biological sample, without the need for amplification of genetic material within the sample.

Figure 4A:
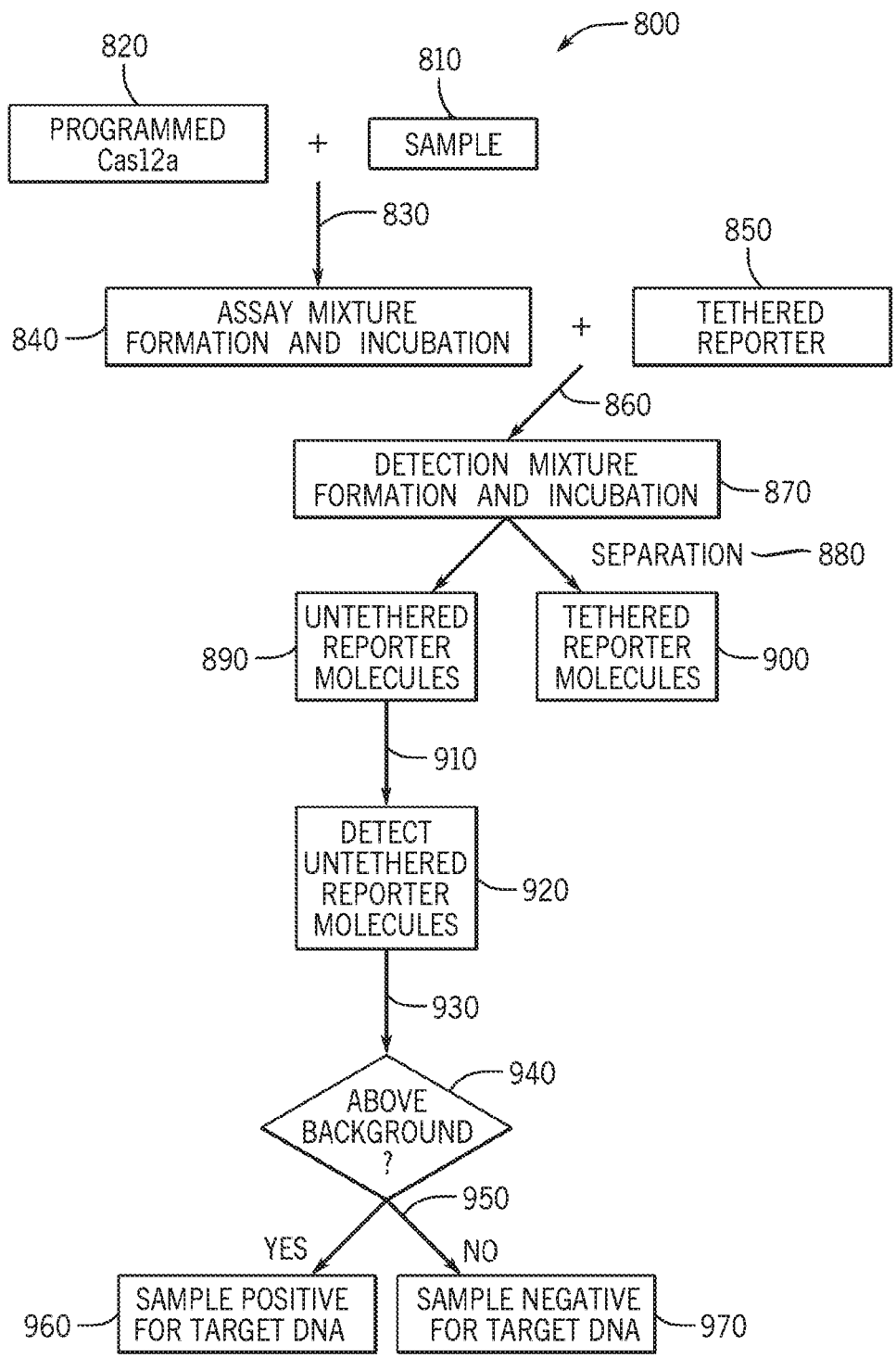
FIGS. 4A and 4B are a flow diagram of an embodiment of the disclosed method (FIG. 4A), and a block diagram of an embodiment of the disclosed system (FIG. 4B).

An embodiment of the disclosed method 800 is depicted as a flow diagram in FIG. 4A. In this embodiment, the Cas protein is a programmed Cas12a protein 820 (including a guide RNA) that is combined 830 with a sample 810 that may or may not include a target DNA sequence, and incubated to create an assay mixture 840. After incubation, the assay mixture 840 is combined 860 with an indicator device 850 comprising a reporter molecule tethered to a solid support via a tether comprising at least one single stranded DNA indicator sequence, to create a detection mixture 870. The detection mixture 870 is incubated for a time to allow cleavage of the indicator sequence. Then tethered reporter molecules 900 are separated 880 from the untethered reporter molecules 890. The untethered reporter molecules 890 may be assayed for a signal 910 and that can be detected 920. The detected signal 930 may be compared 940 to a background value to determine 950 whether the sample is scored as positive 960 or negative 970 for the presence of a target DNA sequence. Still other embodiments, as described above, at FIGS. 3A and 3B, may include untethering of a first reporter molecule from a first indicator device, and untethering of a second from a second indicator device.

The disclosed methods are useful for assaying a variety of samples, including biological samples from a human or non-human source. In some embodiments, the samples may be selected or derived from one or more of blood, sweat, plasma, serum, sputum, saliva, mucus, cells, excrement, urine, cerebrospinal fluid (CSF), breast milk, semen, vaginal fluid, tissue, etc. Target nucleic acid sequence detectable by the disclosed methods may be derived from a variety of sources or may be synthetically produced. Where the target nucleic acid sequence is biologically derived, the source may be one or more of a fungus, bacterium, virus, protozoa, eukaryote, mammalian cell, or human cell.

The disclosed methods may use a variety of detection methods to determine the presence or absence of a target nucleic acid sequence. Detection may be direct or indirect detection of a reporter molecule untethered from the solid support. Suitable reporter molecules may include, without limitation, one or more of a fluorescent molecule, a luminescent molecule, a fusion protein, a protein, an enzyme, a fluorescent or luminescent protein, a SERS particle, or a nanoparticle. Suitable reporter molecules may result in a signal that is detectable by one or more of Raman spectroscopy, fluorescence spectroscopy, spectroscopy, electrochemical methods, visual inspection (for example, color, turbidity), or surface Plasmon resonance. In some embodiment, the disclosed methods may include a step that may result in untethering a reporter molecule from a solid support. In some embodiments, the solid support may be selected from one or more of a fiber or bead including, without limitation, one or more of cellulose, agarose, acrylamide, dextran, or a metal. In some embodiments, a plurality of tether molecules may be attached to the solid support, and a plurality of reporter molecules may be attached to a single tether molecule. In some embodiments, the tether molecule may include one or more of PEG, DNA, streptavidin, biotin, maleimide, sulfur, thiol, amino acids, proteins, succinimide, bacterial protein, haloalkane dehalogenase (HaloTag), chloroalkane, triazol, sulfone, and the tether molecule is covalently attached to the solid support and/or the reporter molecule.

Systems

Also disclosed are systems for determining a presence of a target nucleic acid sequence. An embodiment of the disclosed system may include a modified Cas molecule, a device including a tether, a reporter molecule, and a solid support, wherein the tether has at least one indicator nucleic acid sequence, the Cas protein is "programmed" and includes a guide nucleic acid sequence complementary to the target nucleic acid sequence. The system may further include an assay compartment, a detection compartment, and a filter positioned between the assay compartment and the detection compartment, wherein the filter is permeable to an untethered reporter molecule. In many embodiments, the system may further include at least one detector configured to detect a signal from an untethered reporter within the detection area.

Figure 4B:
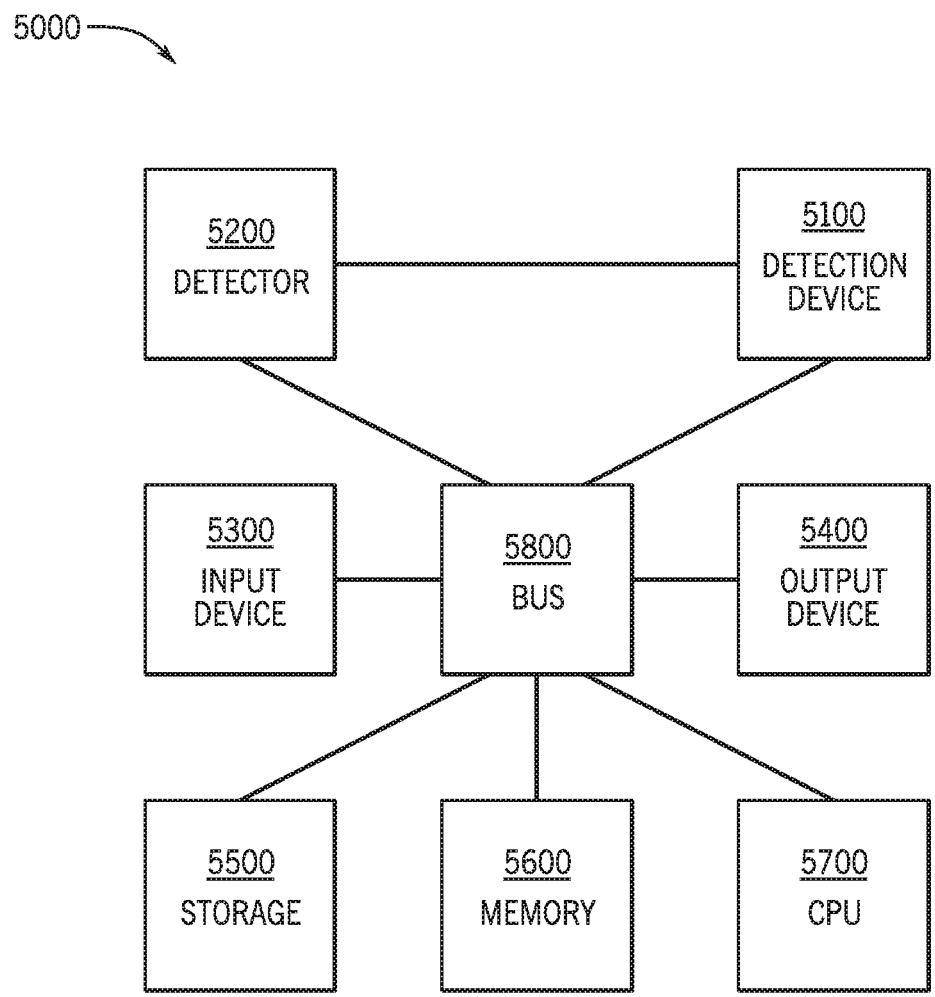

In some embodiments, the system may include a digital computer as shown in FIG. 4B. The system 5000 may include a detection device 5100, and at least one detector 5200 configured to detect a signal from an untethered reporter within a detection area of the detection device 5100. The system may further include an input device 5300, an output device 5400, a storage device 5500, a memory unit 5600, and a digital computer 5700 (or central processing unit, CPU), all of which may be in electrical communication with a bus 5800. The detector and detection device may be in direct communication, for example light or electrical communication. The CPU may include processing electrical circuitry configured for accepting a signal from the detector and processing the signal. The input and/or output devices may provide for user interface, such as for monitoring the system and/or the signal. In an embodiment, the system may indicate the presence or absence of a target sequence in a given sample.

Such a digital computer is well-known in the art and may include one or more of a central processing unit, one or more of memory and/or storage, one or more input devices, one or more output devices, one or more communications interfaces, and a data bus. In some embodiments, the memory may be RAM, ROM, hard disk, optical drives, removable drives, etc. In some embodiments, storage may also be included in the disclosed system. In some embodiments, storage may resemble memory that may be remotely integrated into the system.

The disclosed system may further include at least one output device, for example one or more monitors, display units, video hardware, printers, speakers, etc. In some embodiments, at least one output device is a monitor for viewing the diagnostic video. One or more input devices may also be included, for example pointing devices (e.g., mouse), text input devices (e.g., keyboard), touch screen, cameras, detectors, etc. In some embodiments, at least one input device is a detector for receiving a signal resulting from untethered reporter molecules in the detection area. In some embodiments the detector may be a single wavelength or broad spectrum detector.

The disclosed system may further include at least one communications interfaces, such as LAN network adapters, WAN network adapters, wireless interfaces, Bluetooth interfaces, modems and other networking interfaces.

The disclosed system may further include one or more data buses for communication among the various parts of the disclosed system, for example input/output buses and bus controllers.

In some embodiments, the disclosed system may comprise one or more distributed computers, and may be implemented in various types of software languages including, without limitation C, C++, COBOL, Java, FORTRAN, Python, Pascal, among others. The skilled artisan may compile various software source codes into executable software for use with the disclosed system.

Methods for Detecting a Target Nucleic Acid Sequence

Various methods for detecting a target nucleic acid sequence in a sample are disclosed. In an embodiment, the method may include (i) combining a sample with a Cas protein, wherein the Cas protein includes a guide RNA having a spacer sequence that is complementary to a target sequence of interest, to create an assay mixture, (ii) incubating the assay mixture to allow a target nucleic acid in the sample to hybridize to the spacer sequence, (iii) combining the assay mixture with the described device to create a detection mixture, (iv) incubating the detection mixture, (v) applying a force to the detection mixture sufficient to separate an untethered reporter molecule from a solid support in the device; and (v) detecting the untethered reporter.

The disclosed method may include combining a Cas protein with the sample, which may be a test sample that may or may not include a target nucleic acid sequence. In these embodiments, the Cas protein includes a guide RNA sequence. In some embodiments, the method includes a step of combining the Cas protein with a guide RNA sequence prior to combining it with the sample. In various embodiments, the sample may be combined with a plurality of Cas proteins may include a plurality of guide RNAs of the same or different sequence. In these embodiments, the method may be able to detect the presence of one or more target sequences in a sample. The Cas protein is combined with the sample to create an assay mixture. As described below, the sample may be other than a test sample, for example the sample may be a control sample (known to have no target nucleic acid sequences) or a standard sample having a known amount of target sample.

Samples may be obtained from various sources, and may include various nucleic acid sequences. In some embodiments, the sample may be obtained from a biological, environmental, or synthetic source. A biological sample may include, for example, a tissue, cell, or a bodily fluid from a subject, as well as lysates thereof. In many of these embodiments, the subject may be human, non-human, eukaryotic, prokaryotic, etc. Samples may also be obtained from agricultural and veterinary subjects, including plants and animals. Samples that are environmental may be obtained from foodstuffs, industrial, commercial, medical, and environmental surfaces, air samples, and water samples. In some embodiments, bodily fluid may include blood, sputum, serum, plasma, urine, sweat, saliva, mucus, cells, organelles, etc.

A programmed Cas protein may be combined with the sample and incubated for any suitable times. In some embodiments, the sample is incubated with the Cas protein for less than about 2 hrs., 90 min., 60 min., 40 min., 30 min., 20 min., 10 min., 5 min., 4 min., 3 min., 2 min., 1 min., 55 sec., 50 sec., 40 sec., 30 sec., 20 sec., or 10 sec., and more than about 5 sec., 10 sec., 20 sec., 30 sec., 40 sec., 50 sec., 60 sec., 2 min., 3 min., 4 min., 5 min., 10 min., 20 min., 30 min., 40 min., 50 min., 60 min., or 90 min.

The assay mixture may be incubated under various conditions to allow a target nucleic acid sequence, if present in the sample, to hybridize to the spacer sequence of the guide RNA. In some embodiments, the conditions are designed to aid in hybridization of RNA-RNA, RNA-DNA, or DNA-DNA sequences (e.g. spacer RNA sequence to target nucleic acid sequence), wherein the sequences are 100% complementary. In other embodiments, the conditions for incubation of the assay mixture may be varied to allow for less than 100% complementarity between the spacer sequence and the target sequence, for example 1 mismatch between target nucleic acid and spacer RNA, or less than about 2 mismatches, 3 mismatches, 4 mismatches, or 5 mismatches. In some embodiments, hybridization between a target DNA and a guide RNA may activate non-specific DNase activity of a Cas12a protein, when complementarity is greater than about 80%.

Target sequences may be any single-stranded or double-stranded nucleic acid sequence, for example single-stranded or double-stranded DNA. The target sequence may be derived from coding or non-coding DNA, cDNA, mRNA, tRNA, rRNA, iRNA, miRNA, coding and non-coding RNA. In some embodiments, the target nucleic acid is derived from a pathogen such as a microbe, bacterium, fungus, or virus.

The assay mixture, which may or may not include an activated Cas protein, may be combined with an indicator device, as described above, to create a detection mixture. In some embodiments, the detection mixture is designed to allow an activated Cas protein to cleave an indicator nucleic acid sequence. In an embodiment, the indicator sequence is selected from single-stranded and double-stranded DNA. In some embodiments, an activated Cas protein will cleave an indicator sequence in the tether of the device. Incubation conditions may be selected to reduce cleavage of the indicator sequence by Cas proteins that have not been activated, and by non-Cas proteins with DNase activity.

Nuclease inhibitors may be present in the assay mixture. In some embodiments, the assay mixture may include one or more molecules that inhibit non-Cas12a-dependent DNase activity, but do not affect DNase activity by activated Cas12a proteins. For example, the inhibitor may inhibit mammalian, bacterial, or viral DNases. In some embodiments, the DNase inhibitor may be added to the sample to help preserve a target nucleic acid sequence. In these embodiments, the method may include a step of adding one or more DNA preserving compounds to the sample, for example one or more DNase inhibitors.

The detection mixture may be incubated under various conditions that may aid in cleavage of the indicator sequence in the tether. In some embodiments, the incubation conditions may help to enhance the activity of an activated Cas protein, while minimizing activity of other enzymes. In some embodiments, incubation conditions may promote cleavage of all or substantially all of the tethers present in the detection mixture, to help optimize the concentration of untethered reporter molecules.

A force may be applied to the detection mixture after sufficient incubation, to aid separating tethered and untethered reporter molecules. In these embodiments, the device may include a filter or the detection mixture may be transferred to a second separation device comprising a filter or membrane, permeable to untethered reporter molecules but not to the solid support and tethered reporter molecules. The separating force may allow for movement or translocation of an untethered reporter molecule away from the solid support. The separating force may also aid in translocating untethered reporter molecules by or through a filter or membrane into a detection area.

The separating force may be the result of one or more of magnetic, gravitational, fluid, gas, or other forces. In some embodiments, the force may be applied by subjecting the detection mixture to centrifugation. In these embodiments, centrifugation may provide the force necessary for fluid in the detection mixture to traverse a filter or membrane. In these embodiments, untethered reporter molecules (and other suitable solutes) may flow through the filter or membrane and enter the detection area. In these embodiments, the detection area may be part of a detection device that may be a test tube, for example a microfuge tube. In other embodiments, the detection device may be a multi-well plate.

In some embodiments, the device or detection device may be a lateral flow assay device. In these embodiments, untethered reporter molecules may traverse a filter, membrane, or pad as solvent from the sample is drawn toward a wicking pad.

Detecting the untethered reporter may be achieved in various ways. In most cases, the untethered reporter molecule is translocated to a detection area for detecting. In these embodiments, the detecting area may include a substrate that may be used to detect the presence of the reporter molecule. In other embodiments, the detecting area may include one or more molecules that may aid in concentrating and/or localizing the reporter molecule. In some embodiments, the reporter molecule may, directly or indirectly, produce a signal that may be detected by various means. In some embodiment, for example wherein the reporter molecule is an enzyme, the signal may be colorimetric, fluorescent, or luminescent. In other embodiments, for example wherein the reporter molecule is a fluorophore, nanoparticle, or includes a dye molecule, the signal may be absorbance and/or emission of light at a particular wavelength. In some embodiments the signal may be detected by visual inspection, microscope, or light detector.

The presence of a target sequence may be determined if the signal in the detection area is greater than a background signal. In these embodiments, a background signal may be determined from a sample that is known to contain no target sequence, or where the target sequence has been purposely destroyed by addition of one or more nucleases or compounds. Detecting a signal above the background signal may indicate the presence of a target sequence in the sample, where detecting no signal or a signal below the background signal may indicate no target sequence is present in the sample.

Methods for Quantification of a Target Sequence in a Sample

In some embodiments, the disclosed devices and methods may be used to detect a target nucleic acid sequence in a biological sample and provide quantitative or qualitative information regarding the abundance of the target nucleic acid sequence. In these embodiments, the signal detected from the methods described above may be compared to a background signal and/or standard signals. A standard signal may be the result of a sample containing a known amount of reporter molecule, a known amount of target sequence, or both. In an embodiment, the reporter in the standard sample may be attached to a tether, part of a tether, or may be free of any other molecules. In some embodiments, a target sequence may be included in a standard sample, for example where the reporter is an enzyme. In an embodiment, the target sequences may be the same as, or different than, the target sequence in a test sample. A test sample is a sample obtained from a subject, patient, or source wherein the presence of a target sequence is unknown.

Quantifying the amount of target nucleic acid sequence in a test sample may include a step of measuring signal produced from untethered reporter from a standard sample having a known concentration of a target nucleic acid sequence. In these embodiments, the standard sample may include the same target nucleic acid sequence being assayed in the test sample, or it may be a reference target nucleic acid sequence that is different than the target nucleic acid sequence that may or may not be present in the test sample. In these embodiments, the guide RNA sequence is complementary to the reference nucleic acid sequence. Comparing signals produced by standard samples to a test sample may aid in determining the amount of target nucleic acid sequence in a test sample. If the detected signal is greater than a background value, the target nucleic acid sequence is present in the biological sample, and the signal may then be compared to one or more standard samples to determine the quantity of target nucleic acid sequences in the test sample.

Levels of Target Sequence for Detecting a Signal

The disclosed devices and methods are useful for specifically and sensitively detecting a target nucleic acid sequence in various samples. In some embodiments, the disclosed devices and methods may detect a target nucleic acid sequence in a sample, wherein the concentration of target nucleic acid sequence is less than about $1\times10^{-6}$ M, for example less than about $100\times10^{-9}$ M, $10\times10^{-9}$ M, $1\times10^{-9}$ M, $100\times10^{-12}$M, $10\times10^{-12}$M, $1\times10^{-12}$ M, $100\times10^{-15}$ M, $10\times10^{-15}$ M, $1\times10^{-15}$ M, $100\times10^{-18}$ M, $10\times10^{-18}$ M, or $1\times10^{-18}$ M. The concentration of target nucleic acid in a sample may be quantitated by measuring the amount of a signal detected in the detection area as a result of the untethered reporter molecule.

Kits for Detecting and/or Quantitating the Level of Target Sequence

The disclosed devices and methods may be used with kits, such as test kits, for detecting pathogen infection, including active infection, in a variety of samples. In some embodiments, the sample may be derived from a chronically-infected subject or individual (human or non-human). In some embodiments, the kits may help provide a level of infection by quantitation of the amount of target nucleic acid sequence in the sample. In some embodiments, the kit may include one or more of a guide RNA sequence, and a Cas protein. In some embodiments, one or more Cas proteins are provided, wherein the Cas protein is bound to a guide RNA sequence. In these embodiments, the guide RNA sequences may be the same for each different Cas protein, and therefore the kit may be able to recognize and/or differentiate between two or more target sequences. In other embodiments the kit may include one or more nucleic acids encoding for the Cas protein and guide RNA. The kit may further include device comprising at least a reporter molecule tethered to a solid support, wherein the tether includes at least one indicator sequence. The kit may further include a detection device having a detection area, which may include one or more substrate molecules that may interact with untethered reporter molecules.

Method of Making a Device for Detecting a Target Sequence

Disclosed herein are methods of constructing devices for determining the presence of a target nucleic acid sequence, the method comprising: synthesizing a tether molecule having, a first end, a second end, and at least one indicator sequence positioned between the first and second end. In some embodiments, the at least one indicator sequence may be synthesized with one or more molecules at the 3' or 5' end, and at least two thymine bases in between. The tether may be attached to a reporter molecule at the first end of the tether molecule, and a solid support at the other. In some embodiments, the molecules at the 3' and/or 5' end may be anchor molecules for attaching directly to the reporter molecule and solid support, in other embodiments, additional molecules may be positioned between the tether and reporter molecule or solid support. In some embodiments, the step of attaching of the solid support or the at least one reporter molecule includes covalently attaching to the tether by one or more of a cysteine linkage or amine linkage.

Detection Devices

The disclosed tethered reporter molecule may be included in a detection device that further includes a filter or membrane useful in separating untethered reporter molecules from tethered reporter molecules. The detection devices may further include a detection area in a detection compartment and an assay area in an assay compartment. In some embodiment, the assay area and detection area may be separated by one or more filters or membranes, wherein the filter or membrane is permeable to the untethered reporter molecule by not to a tethered reporter molecule. In some embodiments the reporter molecule may be tethered to the filter or membrane to prevent untethered reporter molecules from entering the detection area or detection compartment.

EXAMPLES

Example 1

Lba Cas12a A488-ssDNA Cleavage Assay

Experiments were performed to examine the ability of guide RNA and activator DNA to stimulate Cas12 to cleave an indicator ssDNA sequence. Specifically, a Cas12a/Guide RNA/Target DNA mixture was mixed with an A488-ssDNA-mag bead, and the amount of A488 released upon ssDNA cleavage was quantified. This DNase assay was performed according to manufacturer's protocol with modification.

The following materials were prepared. Cas12a from Lba (Cpf1: EnGen® from New England BioLabs #M6053T) was supplied at 100 μM and stored at −20° C. Three guide RNA samples (G1, G2, and G3) were obtained from IDT and diluted to 100 μM in DEPC-treated water (CRI-17, Guide1 or G1, UAAUUUCUACUAAGUGUAGAUCGUCGCC-GUC CAGCUCGACC (SEQ ID NO: 2); CRI-18 Guide2 or G2, UAAUUUCUACUAAGUGUAGAUGAUCGUUA-CGCUAACUAUGA (SEQ ID NO: 3); CRI-19, Guide3 or G3, UAAUUUCUACUAAGUGUAGAUCCUGGGU-GUUCCACAGCUGA (SEQ ID NO: 4) as follows. 7.2 nmol of CRI-17/G1 was diluted in 72 μL DEPC-treated water. 11.2 nmol of CRI-18/G2 was diluted in 112 μL DEPC-treated water. 10.2 nmol of CRI-19/G3 was diluted in 102 μL DEPC-treated water. 5 μL of each guide RNA sequence mixtures was further diluted 20-fold in DEPC-treated water to provide 100 μL of 5 μM final working stocks. Original and working stocks of guide RNA sequence mixtures were stored at −80° C. until use.

100 μM solutions of target dsDNA (Activator sequences; A1, A2, A3) were also prepared. Specifically, sense and antisense oligonucleotides were obtained from the manufacturer as hybridized duplexes and prepared as follows. 66.9 nmol of the CRI-20 sense and anti-sense duplexes (sequences) ((Activator1 or A1=GCTTGTGGCCGTTTA-CGTCGCCGTCCAGCTCGACCAGGATGGGCAC-CACCCCGGC (SEQ ID NO: 5)+GCCGGGGTGGTGCC-CATCCTGGTCGAGCTGGACGGCGACGTAAACGGC-CACAAGC (SEQ ID NO: 6)) were diluted in 669 μL DEPC-treated water to give 100 μM. 90.4 nmol of CRI-21 (Activator2 or A2=GACGACAAAACTTTAGATCGTTA-CGCTAACTATGAGGGCTGTCTGTGGAATGCTA (SEQ ID NO: 7)+TAGCATTCCACAGACAGCCCTCATAGT-TAGCGTAACGATCTAAAGTTTTGTCGTC (SEQ ID NO: 8)) was diluted in 904 μL DEPC-treated water to give 100 μM; and 71.3 nmol of CRI-22 (Activator3 or A3=AGTTGTGTTAGTTTACCTGGGTGTTCCACAGC-TGATAGTGATTGCCTTGAATAAA (SEQ ID NO: 9)+TT-TATTCAAGGCAATCACTATCAGCTGTGGAACACC-CAGGTAAACTAACACAACT (SEQ ID NO: 10)) was diluted in 713 μL DEPC-treated water to give 100 μM. Next, 1 μL of each ds Target/Activator sequence was diluted 100-fold in DEPC-treated water to give 1 μM final working stocksOriginal and working stock solutions were stored at −20° C. until use.

Streptavidin magnetic beads (SA-Mag beads) bound with a green fluorescein dye (A488) covalently attached to a biotinylated ssDNA were prepared as suggested by the manufacturer as follows. Briefly, 20 μL containing 2 mg of MyOne™ Streptavidin Cl Dynabeads™, prepared for RNA applications, was incubated with 2000 pmol ssDNA at room temperatures for 16 hrs, then washed extensively to remove unbound ssDNA. Beads were quantified and showed to contain ssDNA of sequence CRI-13 (TTATT) at approx. 201 pmol/mg of bead and ssDNA of sequence CRI-14 (TTAT-TTTATT) (SEQ ID NO: 1) at approx. 433 pmol/mg of bead and stored at 4° C.

Cas12a DNase assays were performed in a buffer as suggested by the manufacturer (NEB) and elsewhere (Chen et al., Science 2018): Assay buffer contains 50 mM NaCl, 10 mM Tris-HCl, pH 7.9 @ 25° C., 10 mM MgCl$_2$, 100 μg/mL BSA, and 1 mM DTT, and was prepared (as in Chen et. al., Science 2018) from stocks of 1 M MgCl$_2$, 1 M Tris pH 7.5, 5 M NaCl, 20 mg/mL BSA, 1 M DTT and DEPC-treated water, kept on ice prior to use, and stored at −20° C. Reactions were performed in 48-well unskirted, low-profile plates (BIO-RAD Multiplate PCR plate, Cat. no. MLL4801.

Assays were performed as follows. Guide RNA and Target DNA was prepared as described above, thawed and kept on ice until use. 100 μM of the Cas12a stock was removed from −20° C. storage and kept on ice until use. 4× Cas12a, Guide RNA, Activator DNA solutions were prepared: as follows: 0.5 μL of 100 μM Cas12a was diluted with 250 μL of buffer (4×=200 nM Cas12a); 1.0 μL of 5 μM Guide RNA was diluted with 24 μL of buffer (4×=200 nM Guide RNA); 1.0 μL of 1 μM Activator DNA was diluted with 249 μL of buffer (4×=4 nM Activator DNA)). Below is a table, TABLE 1, depicting added components for various wells of the assay plate.

TABLE 1

| Plate 5 μL of each 4x Cas12a, Guide RNA, Activator DNA according to: | | | |
|---|---|---|---|
| Row | Enzyme | Guide RNA | Activator DNA |
| A | − | − | − |
| B | + | − | − |
| C | + | G1 | − |
| D | + | G1 | A1 |
| E | + | G2 | − |
| F | + | G2 | A2 |
| G | + | G3 | − |
| H | + | G3 | A3 |

Magnetic beads were prepared as follows. Stocks of CRI-13 containing beads or CRI-14 containing beads were diluted into 1 mL buffer at RT prior to preparation of other reagents. Beads were then collected by exposure to a magnet for 2 mM, then supernatant was removed and discarded, before resuspending the beads in 40 μL of buffer (at 4×=400 nM ssDNA substrate). 5 μL beads was added to each well to initiate the reactions. The plate was sealed with clear, adhesive film, and immediately placed at 37° C. with end-over-end rocking. After 60 mM, the plate was pulsed in a PCR plate spinner, and the beads collected on a 24-post magnet for 2 mM. All supernatant was then carefully removed and assayed as described below.

A488 Assay

A 10 μM standard was created using the A488 tethered to ssDNA (A488-ssDNA, either CRI-13 or CRI-14), which was stored at −20° C. The A488 standard was prepared in buffer as follows. 12.5 μL of 10 μM ssDNA was diluted into 112.5 μL buffer to produce a 1000 nM standard solution. This 1000 nM standard solution was then serially diluted 10-fold four times to create five solutions containing 1000 nM, 100 nM, 10 nM, 1.0 nM, and 0.1 nM of ssDNA standard. 10 μL of each test solution was combined with 90 μL buffer and plated along with 100 μL of standards for comparison in flat-bottom, opaque-walled plates for fluorescence detection.

Plates were read in a BIOTEK GenS Synergy H1 plate reader at T=22° C., after orbital shaking for 1 min. Ex/Em wavelengths 490/525 were used for collecting fluorescence emission.

Figure 5:
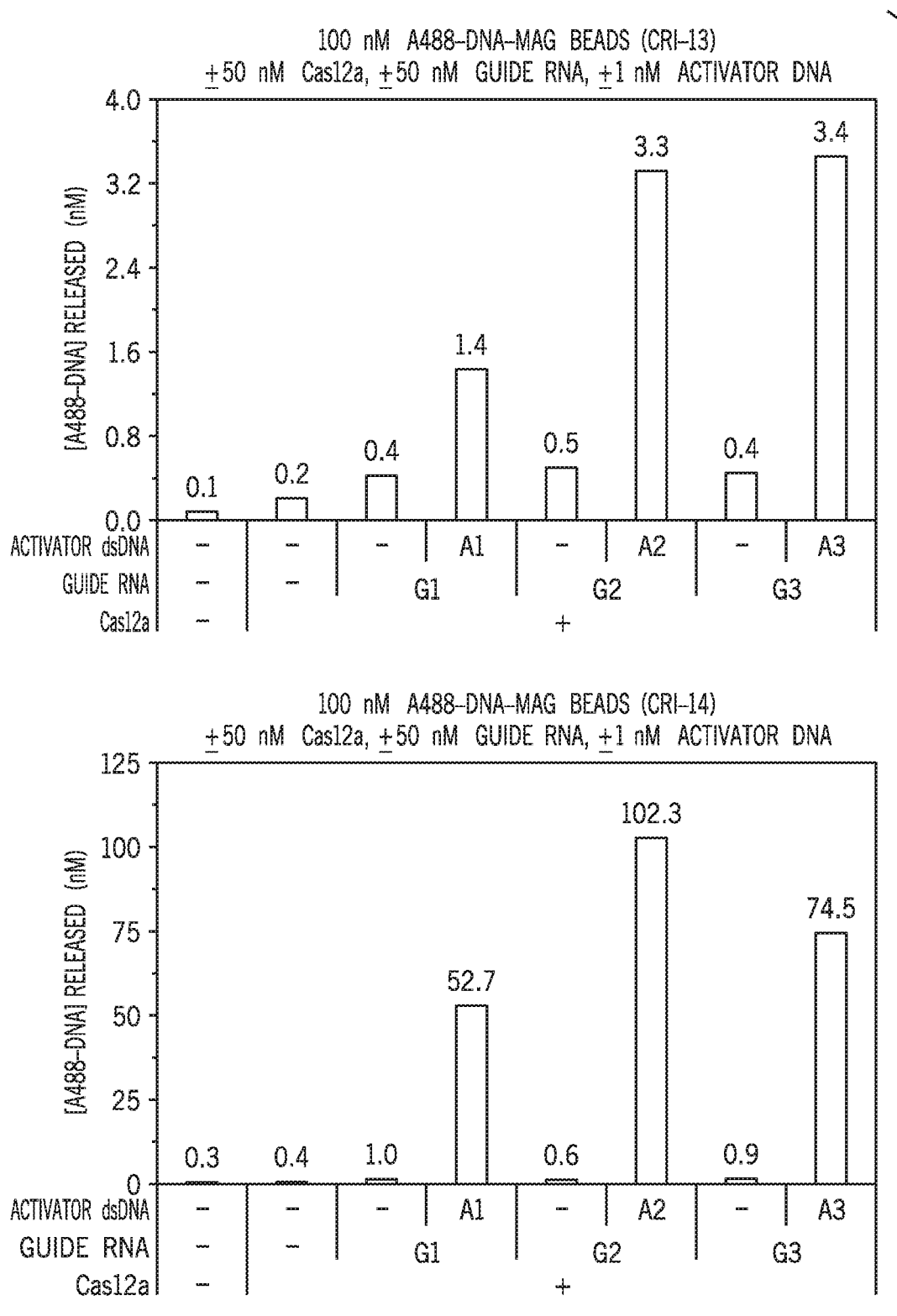
FIG. 5 shows results from Example 1, in the form of a bar graph, from assays with A488 as reporting molecule.

Results from these experiments are shown at FIG. 5. As shown in the bar graphs presented in FIG. 5, in the presence of Guide ssRNA and Activator dsDNA, Cas12a is able to cleave the single stranded DNA oligonucleotide connecting the A488 fluor to the magnetic bead. FIG. 5 also demonstrates that the A488 signal from the beads is considerably above background—that is the signals from lanes marked −Cas12a, −Guide RNA, −Activator dsDNA and +Cas12a, +Guide RNA, − Activator dsDNA, were both considerably less than those comprising+Cas12a, +Guide RNA, +Activator dsDNA. It was also observed that the Cas12a used in these studies cleaved ssDNA indicator sequences comprising the sequence TTATT at a considerably lower efficiency (CRI-13, upper graph; 1.4-3.4 nM released) than cleavage of the longer ssDNA indicator comprising two TTATT sequences (CRI-14, lower graph; 52.7-102.3 nM released). This was in contrast to DNaseI, which showed that CRI-14 was cleaved at roughly twice the efficiency of CRI-13 (not shown). FIG. 5 also indicates that the pairing of Guide2/Activator2 is more efficient than the other two pairs (Gude1/Activator) or Gude3/Activator3) in stimulating DNase activity of Cas12a against the longer bridge. However, Gude2/Activator2 appears to be roughly equivalent to Guide3/Activator3 ability to activate Cas12a DNase activity on the shorter bridge. Guide1/Activator) is least potent in both assays.

Example 2

Lba Cas12a A488-ssDNA Cleavage Assay to Analyze Guide/Activator Specificity

In these experiments, A488-ssDNA-mag bead DNase assays were performed as in Example 1. Briefly, Lba Cas12a was obtained from manufacturer (NEB; M6053T) at 100 µM and stored at −20° C. CRI-17 (Guide1), CRI-18 (Guide2), CRI-19 (Guide3) was as described above. CRI-20 (Activator1), CRI-21 (Activator2), CRI-22 (Activator3) was as described above. SA-Mag beads bound with A488 conjugated to ssDNA—specifically CRI-14 as described above. Assay buffer (50 mM NaCl, 10 mM Tris-HCl, pH 7.9 @ 25° C., 10 mM $MgCl_2$, 100 µg/mL BSA, 1 mM DTT), stored at −20° C., was prepared as described above. Again, these DNAse assays were performed in BIO-RAD Multiplate PCR plate (Cat. no. MLL4801) 48-well, unskirted, low profile. Detection of A488 released into supernatants was performed in flat-bottom opaque-walled plates for fluorescence detection and dilution series of an A488 standard comprising ssDNA sequence CRI-14, prepared as described above.

Reagents were thawed on ice prior to performing the assay. 100 µM Cas12a stock was also kept on ice until use. 4× Cas12a, Guide RNA, and Activator DNA mixtures were prepared as follows. 0.5 µL of 100 µM Cas12a was diluted with 250 µL of buffer (4×=200 nM Cas12a); for Cas12a/ EDTA samples, 1 µL of 0.5 M EDTA was diluted with 19 µL of 200 nM Cas12a (4×=200 nM Cas12a, 25 mM EDTA); for Guides 1 and 3: 2.0 µL of 5 µM Guide RNA was diluted with 48 µL of buffer (4×=200 nM Guide RNA); for Guide 2: 6.0 µL of 5 µM Guide RNA was diluted with 144 µL of buffer (4×=200 nM Guide RNA); for Guide/EDTA: 1 µL of 0.5 M EDTA was diluted with 19 µL of 200 nM Guide (4×=200 nM Guide, 25 mM EDTA); for Activators 1-3: 1.0 µL of 1 µM Activator DNA was diluted with 249 µL of buffer (4×=4 nM Activator DNA); for Activator 2 dilutions, serial 10-fold dilutions were prepared: 5 µL Activator was diluted with 45 µL (4×=4000, 400, 40, 4, 0.4, 0.04 pM Activator DNA); for Activator/EDTA: 1 µL of 0.5 M EDTA was diluted with 19 µL of 4 nM Activator (4×=4 nM Activator, 25 mM EDTA).

5 µL of each of 4× Cas12a, Guide RNA, and Activator DNA solution were added to the plates according to TABLE 2, below.

TABLE 2

| Row | Col 1-3 C/G2/±A2 [Activator2] (pM) | Col 4 Cas12a | Guide RNA | Activator DNA | Col 5 Cas12a | Guide RNA | Activator DNA |
|---|---|---|---|---|---|---|---|
| A | 0 | − | − | − | + | G1 | A1 |
| B | 0 | + | − | − | + | G1 | A2 |
| C | 0.01 | − | G2 | − | + | G1 | A3 |
| D | 0.1 | − | − | A2 | + | G3 | A1 |
| E | 1 | + | G2 | A1 | + | G3 | A2 |
| F | 10 | + | G2 | A3 | + | G3 | A3 |
| G | 100 | + | − | A2 | + (+EDTA) | G1 (+EDTA) | A1 (+EDTA) |
| H | 1000 | + (+EDTA) | G2 (+EDTA) | A2 (+EDTA) | + (+EDTA) | G3 (+EDTA) | A3 (+EDTA) |

Magnetic beads comprising ssDNA indicator sequences and A488 were prepared as follows. Stocks of CRI-14-containing beads were diluted into 0.5 mL buffer and allowed to sit at RT during preparation of reagents. Beads were collected by exposure to magnet for 2 mM, and supernatant was removed and discarded. Beads were then resuspended in 210 µL of buffer (at 4×=400 nM). 5 µL of beads were transferred into each well to initiate reactions. In wells containing EDTA, 19 mM of EDTA is achieved, an excess over the 10 mM $MgCl_2$ in the 1× buffer.

Assay plates were sealed with clear, adhesive film, and immediately placed at 37° C. with end-over-end rocking. After 60 mM, plates were pulsed in a PCR plate spinner, and beads collected on 24-post magnet for 2 mM and all supernatant carefully removed.

A488 Assay

A488 quantitative standard was prepared as above. Briefly, A488-ssDNA standards were prepared by diluting 12.5 µL of 10 µM standard solution in 112.5 µL buffer, and then serially diluted FOUR times to create 5 standard solutions of 1000 nM, 100 nM, 10 nM, 1.0 nM, and 0.1 nM ssDNA. 10 µL of each supernatant (diluted with 90 µL of buffer), and 100 µL standard solution was assayed in opaque-walled plates for fluorescence detection.

Readings were taken on a BIOTEK GenS Synergy H1 plate reader as described above (T=22° C., orbital shaking 1 mM, Ex/Em wavelengths 490/525. Results are shown in TABLE 3 below and FIGS. 6-8.

TABLE 3

Release of A488 in response to differing Activator DNA concentrations

| [Activator DNA] (pM) | AVG | SD | CV |
|---|---|---|---|
| 0 | 1.47 | 0.30 | 0.20 |
| 0.01 | 1.54 | 0.17 | 0.11 |
| 0.1 | 1.79 | 0.68 | 0.38 |
| 1 | 1.47 | 0.43 | 0.29 |
| 10 | 2.26 | 0.15 | 0.07 |
| 100 | 15.73 | 1.41 | 0.09 |
| 1000 | 78.79 | 16.70 | 0.21 |

Figure 6:
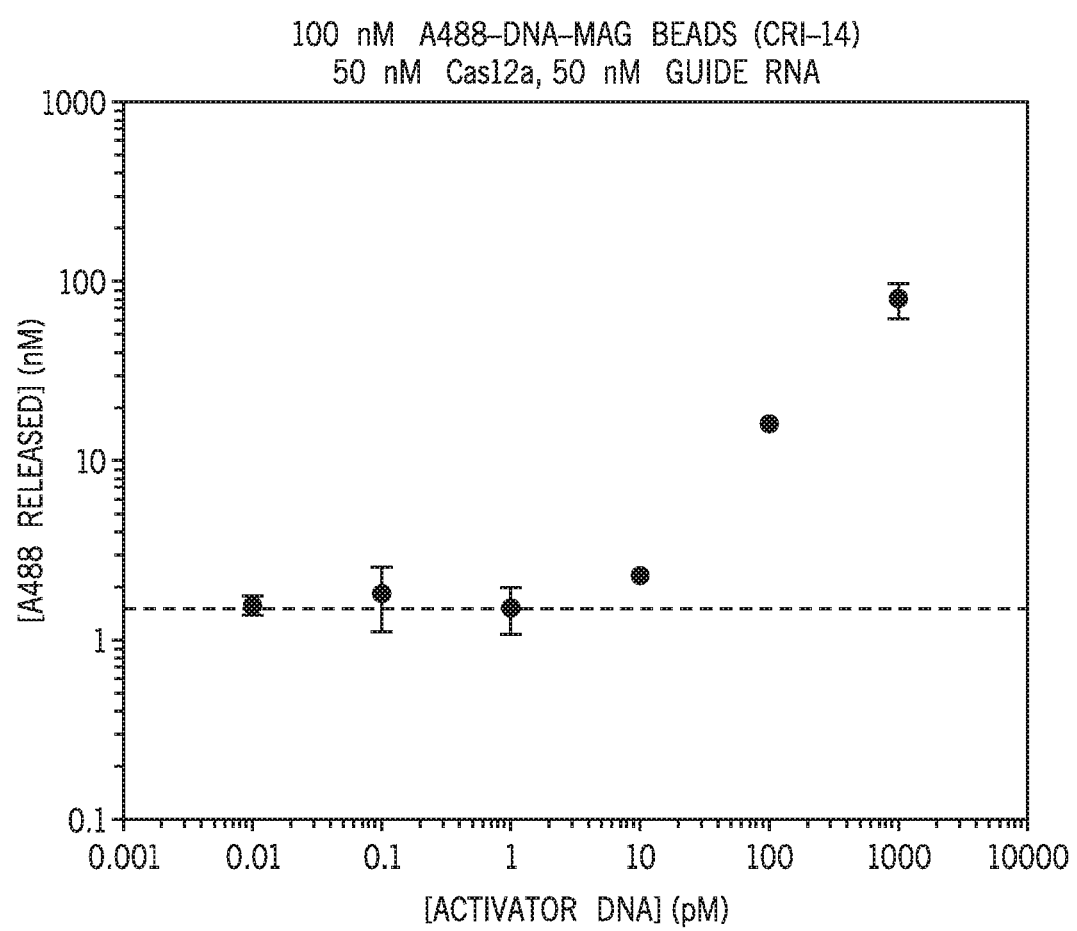
FIG. 6 shows results from A488 assay with increasing concentrations of Activator/Target sequence.
Figure 7:
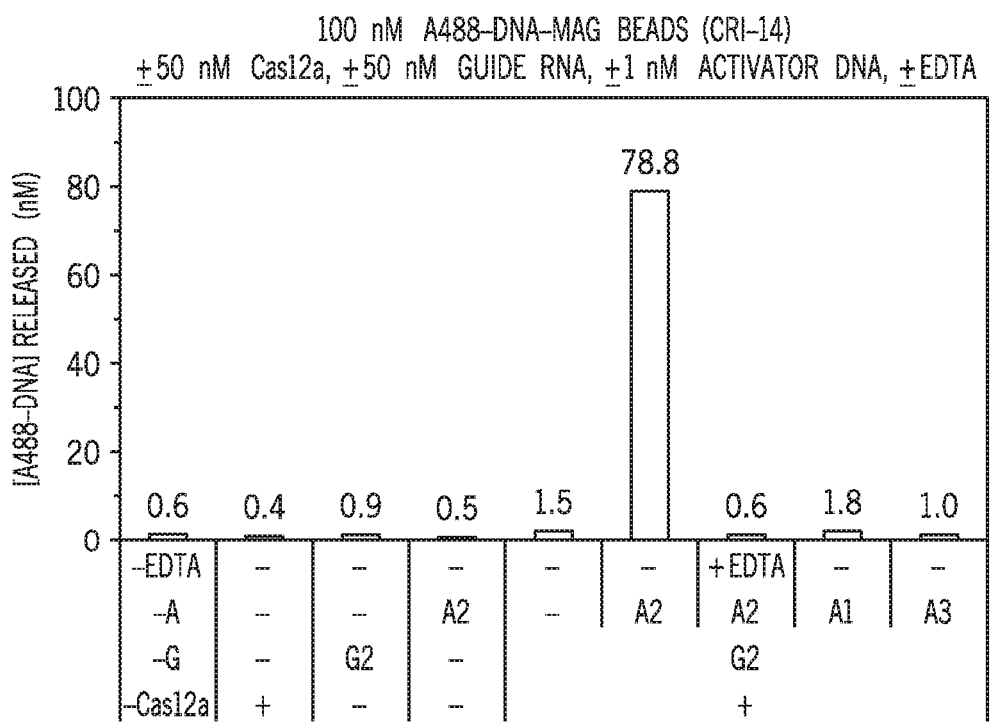
FIG. 7 is a bar graph of results from Example 2 A488 assay.
Figure 8:
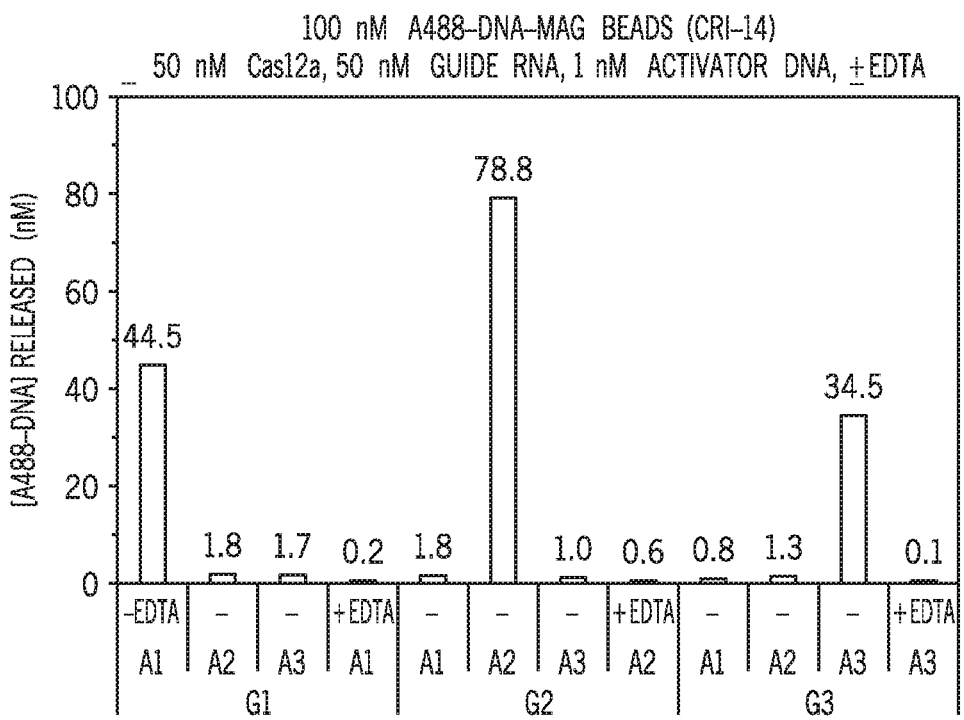
FIG. 8 is a bar graph of results from Example 2 A488 assay.

The limit of detection (LOD) in these assays for Guide2 RNA-activated detection of Activator2 dsDNA was between 1 and 10 pM (FIG. 6). These experiments show that Cas12a cleavage of DNA substrate is (a) dependent on free Mg2+ (since EDTA eliminates activity), and (b) depends upon presence of correct combination of RNA guide and dsDNA target (FIGS. 7-8). As shown above, the greatest activity was observed with the Guide2 RNA/Activator2 combination. However, in these experiments assay Guide1 RNA/Activator1 stimulated more activity than Guide3 RNA/Activator3, the reverse of what was obtained in Example 1 on CRI-14 beads.

This disclosure has been made with reference to various example embodiments. However, those skilled in the art will recognize that changes and modifications can be made to the embodiments without departing from the scope of the present disclosure. For example, various operational steps, as well as components for carrying out operational steps, can be implemented in alternate ways depending upon the particular application or in consideration of any number of cost functions associated with the operation of the system e.g., one or more of the steps can be deleted, modified, or combined with other steps.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, the various aspects and embodiments disclosed herein are for purposes of illustration and are not intended to be limiting, with the true scope and spirit being indicated by the following claims.

The invention claimed is:

1. A system for determining a presence of a target nucleic acid sequence in a sample, the system comprising:
a modified Cas protein complex, including a guide RNA sequence complementary to the target sequence, and a Cas12 endonuclease;
at least one reporter molecule;
a tether molecule having a first end, a second end, and at least one indicator nucleic acid sequence positioned between the first and second end, wherein the at least one reporter molecule is attached at the first end of the tether molecule;
a solid support attached at the second end of the tether molecule;
an assay compartment including the solid support;
a detection compartment; and
a filter positioned between the assay compartment and the detection compartment so that reaction fluid flows through the filter when moving from the assay compartment to the detection compartment, and wherein the filter is permeable to an untethered reporter molecule and impermeable to a tethered reporter molecule.

2. The system of claim 1, wherein the solid support is covalently attached to the tether molecule.

3. The system of claim 1, wherein the Cas12 endonuclease is Cas12a.

4. The system of claim 1, wherein the Cas12 endonuclease is Cas12a and the at least one indicator nucleic acid sequence is single-stranded deoxyribonucleic acid.

5. A method of detecting a target nucleic acid sequence in a biological sample, the method comprising:
combining the biological sample with a composition to create a sample mixture, the composition including at least one modified Cas protein complex including a guide RNA having a sequence complementary to the target sequence, and a Cas12 endonuclease;
incubating the sample mixture with a nuclease detection device to create an assay mixture, the nuclease detection device including;
at least one reporter molecule; and
a tether molecule having a first end, a second end, and at least one indicator nucleic acid sequence positioned between the first and second end, wherein the at least one reporter molecule is attached at the first end of the tether molecule;
a solid support attached at the second end of the tether molecule;
an assay compartment including the solid support;
a detection compartment; and
a filter positioned between the assay compartment and the detection compartment so that the assay mixture flows through the filter when moving from the assay compartment to the detection compartment, and wherein the filter is permeable to an untethered reporter molecule and impermeable to a tethered reporter molecule;
incubating the assay mixture for an assay period;
applying a separating force to the assay mixture; and
detecting a signal from the untethered reporter molecule, wherein if the detected signal is greater than a background value, the target sequence is present in the biological sample, wherein the background value is obtained from a biological sample lacking the target sequence.

6. The method of claim 5, wherein the biological sample is from a human and selected from one or more of blood, sweat, serum, sputum, saliva, mucus, cells, and tissue.

7. The method of claim 5, wherein the target sequence is obtained from a fungus, bacterium, virus, protozoa, or mammalian cell.

8. The method of claim 5, wherein the at least one reporter molecule is selected from one or more of a fluorescent molecule, a luminescent molecule, a fusion protein, a protein, an enzyme, a SERS particle, and a nanoparticle.

9. The method of claim 5, wherein the solid support is a fiber or bead including one or more of cellulose, agarose, acrylamide, dextran, or a metal, with a plurality of tether molecules attached to the solid support.

10. The method of claim 5, wherein the tether molecule includes one or more of PEG, DNA, streptavidin, biotin, maleimide, sulfur, thiol, amino acids, proteins, succinimide, bacterial protein, haloalkane dehalogenase, chloroalkane, triazol, sulfone, glutamine, or lysine, and the tether molecule is covalently attached to the solid support and/or the reporter molecule.

11. The method of claim 5, wherein the separating force is selected from at least one of centrifugation, lateral fluid flow, microfluidic fluid flow, or magnetism.

12. The method of claim 5, wherein the signal is detected by one or more of Raman spectroscopy, fluorescence spectroscopy, luminometer, visual inspection, or surface plasmon resonance.

13. The method of claim 5, further comprising filtering the untethered reporter molecule through a filter before detecting a signal from the untethered reporter molecule.

14. The method of claim 13, wherein the solid support is a filter in a lateral flow device.

15. The method of claim 5 wherein the Cas protein molecule is Cas12a.

16. The method of claim 5, wherein the Cas12 endonuclease is Cas12a and the indicator nucleic acid sequence is single-stranded ribonucleic acid.

17. A method of detecting a target nucleic acid sequence in a biological sample, the method comprising:
obtaining a biological sample;
combining the biological sample with a composition comprising at least one Cas protein complex modified with a guide RNA sequence complementary to the target sequence and a Cas12 endonuclease, to create a sample mixture;
incubating the sample mixture with an indicator device to create an assay mixture, the indicator device including,
a bead of a cross-linked copolymer of copolymer of allyl dextran and N,N'-methylene bisacrylamide;
a tether molecule with a first end, a second end, and at least one indicator nucleic acid sequence positioned between the first and second end, wherein the at least one indicator nucleic sequence includes at least 2 nucleobases, including at least two uracil bases, wherein the first end is attached to the bead; and
at least one luciferase enzyme attached to a second end of the tether molecule,
an assay compartment including a solid support;
a detection compartment; and
a filter positioned between the assay compartment and the detection compartment so that the assay mixture flows through the filter when moving from the assay compartment to the detection compartment, and wherein the filter is permeable to an untethered reporter molecule and impermeable to a tethered reporter molecule;
incubating the assay mixture for an assay period;
applying a centrifugal force to the assay mixture;
forcing at least a portion of the assay mixture through the filter;
allowing an untethered reporter molecule to pass through the filter into a detection compartment including luciferin; and
detecting light produced responsive to oxidation of luciferin by luciferase.

18. The method of claim 17, wherein the Cas12 endonuclease is Cas12a.

19. The method of claim 18, wherein the Cas12 endonuclease is Cas12a and the indicator nucleic acid sequence is single-stranded ribonucleic acid.

20. A system for determining a presence of a target nucleic acid sequence in a sample, the system comprising:
a modified Cas protein complex, including a guide RNA sequence complementary to the target sequence, and a Cas12 endonuclease;
a first indicator device comprising at least one first reporter molecule, a first tether molecule having a first end, a second end, and at least one first indicator nucleic acid sequence positioned between the first and second end, wherein the at least one first reporter molecule is attached at the first end of the first tether molecule;
a second indicator device comprising at least one second reporter molecule, a second tether molecule having a first end, a second end, and at least one second indicator nucleic acid sequence positioned between the first and second end, wherein the at least one second reporter molecule is attached at the first end of the second tether molecule, wherein the at least one second indicator sequence is cleavable by the at least one first reporter molecule;
a solid support attached at the second end of the first and second tether molecules;
an assay compartment including the solid support;
a detection compartment; and
a filter positioned between the assay compartment and the detection compartment, so that reaction fluid flows through the filter when moving from the assay compartment to the detection compartment, and wherein the filter is permeable to an untethered reporter molecule and impermeable to a tethered reporter molecule.

21. The system of claim 20, wherein the Cas12 endonuclease is Cas12a.

22. The system of claim 20, wherein the Cas12 endonuclease is Cas12a and the at least one first indicator nucleic acid sequence is single-stranded deoxyribonucleic acid.

23. The system of claim 20, wherein the first reporter molecule is an enzyme selected from lipase, glyase, nuclease, restriction endonuclease, and protease, and the second indicator sequence is selected from a lipid, carbohydrate, nucleic acid, peptide, and protein.

* * * * *

SEQUENCE LISTING

<160> NUMBER OF SEQ ID NOS: 10

<210> SEQ ID NO 1
<211> LENGTH: 10

```
<212> TYPE: DNA
<213> ORGANISM: Artificial Sequence
<220> FEATURE:
<223> OTHER INFORMATION: Indicator sequence

<400> SEQUENCE: 1
ttattttatt                                                              10

<210> SEQ ID NO 2
<211> LENGTH: 41
<212> TYPE: RNA
<213> ORGANISM: Artificial Sequence
<220> FEATURE:
<223> OTHER INFORMATION: CRI-17 Guide1

<400> SEQUENCE: 2
uaauuucuac uaaguguaga ucgucgccgu ccagcucgac c                           41

<210> SEQ ID NO 3
<211> LENGTH: 41
<212> TYPE: RNA
<213> ORGANISM: Artificial Sequence
<220> FEATURE:
<223> OTHER INFORMATION: CRI-18 Guide2

<400> SEQUENCE: 3
uaauuucuac uaaguguaga ugaucguuac gcuaacuaug a                           41

<210> SEQ ID NO 4
<211> LENGTH: 41
<212> TYPE: RNA
<213> ORGANISM: Artificial Sequence
<220> FEATURE:
<223> OTHER INFORMATION: CRI-19 Guide3

<400> SEQUENCE: 4
uaauuucuac uaaguguaga uccugggugu uccacagcug a                           41

<210> SEQ ID NO 5
<211> LENGTH: 55
<212> TYPE: DNA
<213> ORGANISM: Artificial Sequence
<220> FEATURE:
<223> OTHER INFORMATION: CRI-20 Activator1-1

<400> SEQUENCE: 5
gcttgtggcc gtttacgtcg ccgtccagct cgaccaggat gggcaccacc ccggc            55

<210> SEQ ID NO 6
<211> LENGTH: 55
<212> TYPE: DNA
<213> ORGANISM: Artificial Sequence
<220> FEATURE:
<223> OTHER INFORMATION: CRI-20 Activator1-2

<400> SEQUENCE: 6
gccggggtgg tgcccatcct ggtcgagctg gacggcgacg taaacggcca caagc            55

<210> SEQ ID NO 7
<211> LENGTH: 55
<212> TYPE: DNA
<213> ORGANISM: Artificial Sequence
<220> FEATURE:
<223> OTHER INFORMATION: CRI-21 Activator2-1

<400> SEQUENCE: 7
```

-continued

```
gacgacaaaa ctttagatcg ttacgctaac tatgagggct gtctgtggaa tgcta        55

<210> SEQ ID NO 8
<211> LENGTH: 55
<212> TYPE: DNA
<213> ORGANISM: Artificial Sequence
<220> FEATURE:
<223> OTHER INFORMATION: CRI-21 Activator2-2

<400> SEQUENCE: 8
tagcattcca cagacagccc tcatagttag cgtaacgatc taaagttttg tcgtc        55

<210> SEQ ID NO 9
<211> LENGTH: 55
<212> TYPE: DNA
<213> ORGANISM: Artificial Sequence
<220> FEATURE:
<223> OTHER INFORMATION: CRI-22 Activator3-1

<400> SEQUENCE: 9
agttgtgtta gtttacctgg gtgttccaca gctgatagtg attgccttga ataaa        55

<210> SEQ ID NO 10
<211> LENGTH: 55
<212> TYPE: DNA
<213> ORGANISM: Artificial Sequence
<220> FEATURE:
<223> OTHER INFORMATION: CRI-22 Activator3-2

<400> SEQUENCE: 10
tttattcaag gcaatcacta tcagctgtgg aacacccagg taaactaaca caact        55
```